(12) United States Patent
Krotz et al.

(10) Patent No.: US 7,270,850 B2
(45) Date of Patent: Sep. 18, 2007

(54) MESOPOROUS PERMEATION LAYERS FOR USE ON ACTIVE ELECTRONIC MATRIX DEVICES

(75) Inventors: Jainamma Krotz, San Diego, CA (US); Daniel J. Smolko, Jamul, CA (US); Howard R. Reese, Poway, CA (US); Thomas J. Onofrey, San Marcos, CA (US); Daguang Wang, San Diego, CA (US); Theodore M. Winger, San Diego, CA (US); John R. Havens, San Diego, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 11/082,325

(22) Filed: Mar. 16, 2005

(65) Prior Publication Data

US 2005/0164283 A1    Jul. 28, 2005

Related U.S. Application Data

(63) Continuation of application No. 10/014,895, filed on Dec. 10, 2001.

(51) Int. Cl.
 *C23C 16/00* (2006.01)
 *B01D 29/00* (2006.01)

(52) U.S. Cl. .............. 427/255.28; 210/490; 210/500.1; 210/500.35; 436/172; 435/6; 435/287.2; 204/400; 204/403; 422/68.1; 422/50

(58) Field of Classification Search ........... 210/321.35, 210/490, 500.35; 435/4, 6, 180, 287.2; 536/23.1; 264/41; 427/244, 255.28; 430/311–320; 422/52, 98, 68.1, 50; 204/400, 403; 436/172
See application file for complete search history.

(56) References Cited

U.S. PATENT DOCUMENTS 3,981,671 A    9/1976 Edwards (Continued)

FOREIGN PATENT DOCUMENTS

DE    19705303 A1    1/1998

(Continued)

OTHER PUBLICATIONS

Ogawa, et al., "Preparation Of Self-Standing Transparent Films Of Silica-Surfactant Mesostructured Materials and the Conversion to Porous Silica Films", Adv. Mater., 10, No. 14, 1998, 1077-1080.

(Continued)

*Primary Examiner*—Ana M. Fortuna
(74) *Attorney, Agent, or Firm*—O'Melveny & Myers LLP

(57) ABSTRACT

The present invention provides improved synthetic polymer hydrogel permeation layers for use on active electronic matrix devices for biological assays. The present invention includes methods for forming a permeation layer on an array of microelectrodes including the steps of attaching a linker to the surface of the array by treating the surface with a linker by vapor deposition and providing a polymerization solution that includes at least one monomer having a polymerizable moiety, a modified streptavidin, a surfactant or porogen, and a cross-linking agent. The surface of the array is then contacted with the polymerization solution and the polymerization solution is then polymerized on the surface of the array to form a permeation layer that is attached o the surface of the array through the linker.

34 Claims, 15 Drawing Sheets

U.S. PATENT DOCUMENTS

| | | | |
|---|---|---|---|
| RE30,130 E | 10/1979 | Edwards | |
| 4,205,028 A | 5/1980 | Brueggemann et al. | |
| 4,284,399 A | 8/1981 | Newcomb et al. | |
| 4,472,124 A | 9/1984 | Kashihara et al. | |
| 4,497,763 A | 2/1985 | Monnet | |
| 4,552,633 A | 11/1985 | Kumakura et al. | |
| 4,787,963 A | 11/1988 | MacConnell | |
| 4,897,228 A | 1/1990 | Miwa et al. | |
| 5,026,785 A | 6/1991 | Mage et al. | |
| 5,034,428 A | 7/1991 | Hoffman et al. | |
| 5,104,931 A | 4/1992 | Fleminger et al. | |
| 5,147,297 A | 9/1992 | Myers et al. | |
| 5,151,217 A | 9/1992 | Price | |
| 5,164,162 A | 11/1992 | Ridenour | |
| 5,171,782 A | 12/1992 | Candau et al. | |
| 5,173,147 A | 12/1992 | Shimoyama et al. | |
| 5,200,051 A | 4/1993 | Cozzette et al. | |
| 5,212,050 A * | 5/1993 | Mier et al. | 430/320 |
| 5,217,492 A | 6/1993 | Guire et al. | |
| 5,238,613 A | 8/1993 | Anderson | |
| 5,244,799 A | 9/1993 | Anderson | |
| 5,334,310 A | 8/1994 | Frechet et al. | |
| 5,405,618 A | 4/1995 | Buttery et al. | |
| 5,445,934 A | 8/1995 | Fodor et al. | |
| 5,453,185 A | 9/1995 | Frechet et al. | |
| 5,460,872 A | 10/1995 | Wu et al. | |
| 5,478,893 A | 12/1995 | Ghosh et al. | |
| 5,491,097 A | 2/1996 | Ribi et al. | |
| 5,496,509 A | 3/1996 | Yamamoto et al. | |
| 5,510,074 A | 4/1996 | Rose | |
| 5,521,229 A | 5/1996 | Lu et al. | |
| 5,527,670 A | 6/1996 | Stanley et al. | |
| 5,534,132 A | 7/1996 | Vreeke et al. | |
| 5,543,098 A | 8/1996 | Myers et al. | |
| 5,605,662 A | 2/1997 | Heller et al. | |
| 5,618,265 A | 4/1997 | Myers et al. | |
| 5,624,973 A | 4/1997 | Lu et al. | |
| 5,632,957 A | 5/1997 | Heller et al. | |
| 5,648,482 A | 7/1997 | Meyer | |
| 5,653,939 A | 8/1997 | Hollis et al. | |
| 5,667,667 A | 9/1997 | Southern | |
| 5,744,627 A | 4/1998 | Stowolitz et al. | |
| 5,763,503 A | 6/1998 | Cowperthwaite et al. | |
| 5,770,369 A | 6/1998 | Meade et al. | |
| 5,777,148 A | 7/1998 | Stowolitz et al. | |
| 5,783,054 A | 7/1998 | Raguse et al. | |
| 5,849,486 A | 12/1998 | Heller et al. | |
| 5,889,104 A | 3/1999 | Rosenmayer | |
| 5,919,523 A | 7/1999 | Sundberg et al. | |
| 5,929,208 A | 7/1999 | Heller et al. | |
| 5,952,398 A | 9/1999 | Dietz et al. | |
| 5,981,734 A * | 11/1999 | Mirzabekov et al. | 536/25.3 |
| 6,015,666 A | 1/2000 | Springer et al. | |
| 6,017,696 A | 1/2000 | Heller | |
| 6,031,277 A | 2/2000 | Sugiura et al. | |
| 6,039,897 A | 3/2000 | Lochhead et al. | |
| 6,048,690 A | 4/2000 | Heller et al. | |
| 6,051,380 A | 4/2000 | Sosnowski et al. | |
| 6,054,270 A | 4/2000 | Southern | |
| 6,064,461 A | 5/2000 | Nishida | |
| 6,066,448 A * | 5/2000 | Wohlstadter et al. | 435/6 |
| 6,093,302 A | 7/2000 | Montgomery | |
| 6,099,783 A | 8/2000 | Scranton et al. | |
| 6,099,805 A | 8/2000 | Hartlove | |
| 6,112,908 A | 9/2000 | Michaels | |
| 6,121,027 A | 9/2000 | Clapper et al. | |
| 6,121,489 A | 9/2000 | Dorner et al. | |
| 6,136,444 A | 10/2000 | Kon et al. | |
| 6,143,412 A | 11/2000 | Schueller et al. | |
| 6,197,145 B1 | 3/2001 | Todd et al. | |
| 6,197,881 B1 | 3/2001 | Cosnier et al. | |
| 6,245,249 B1 | 6/2001 | Yamada et al. | |
| 6,245,508 B1 | 6/2001 | Heller et al. | |
| 6,264,825 B1 | 7/2001 | Blackburn et al. | |
| 6,303,082 B1 * | 10/2001 | John et al. | 422/68.1 |
| 6,306,348 B1 * | 10/2001 | Havens et al. | 422/68.1 |
| 6,306,594 B1 * | 10/2001 | Cozzette et al. | 435/6 |
| 6,444,111 B1 | 9/2002 | Montgomery | |
| 6,458,547 B1 | 10/2002 | Bryan et al. | |
| 6,458,584 B1 | 10/2002 | Mirzabekov et al. | |
| 6,524,517 B1 | 2/2003 | John et al. | |
| 6,615,855 B2 | 9/2003 | Lopez et al. | |
| 6,673,433 B1 | 1/2004 | Saeki et al. | |
| 6,673,533 B1 * | 1/2004 | Wohlstadter et al. | 435/6 |
| 6,682,899 B2 * | 1/2004 | Bryan et al. | 435/7.1 |
| 6,689,473 B2 * | 2/2004 | Guire et al. | 428/412 |
| 6,767,816 B2 | 7/2004 | Kleveland et al. | |
| 6,824,974 B2 * | 11/2004 | Pisharody et al. | 435/4 |
| 6,838,053 B2 * | 1/2005 | John et al. | 422/68.1 |
| 6,960,298 B2 | 11/2005 | Krotz et al. | |
| 2002/0014409 A1 | 2/2002 | Matsumoto et al. | |
| 2002/0195345 A1 | 12/2002 | Bentsen et al. | |
| 2003/0146145 A1 | 8/2003 | Krotz et al. | |
| 2003/0190632 A1 | 10/2003 | Sosnowski et al. | |
| 2003/0215937 A1 | 11/2003 | Matson | |
| 2004/0071767 A1 | 4/2004 | Ceve et al. | |
| 2005/0266456 A1 | 12/2005 | Williams et al. | |

FOREIGN PATENT DOCUMENTS

| | | |
|---|---|---|
| EP | 0047645 B1 | 11/1984 |
| EP | 0226470 A2 | 6/1987 |
| EP | 0243501 A1 | 11/1987 |
| EP | 0446040 B1 | 11/1994 |
| JP | 55-152027 A | 11/1980 |
| JP | 56-167419 A | 12/1981 |
| JP | 59-215838 A | 12/1984 |
| JP | 59-227131 A | 12/1984 |
| JP | 01163049 A | 6/1989 |
| JP | 02292013 A | 12/1990 |
| WO | WO93/22678 A2 | 11/1993 |
| WO | WO96/07917 A1 | 3/1996 |
| WO | WO99/29711 A1 | 6/1999 |

OTHER PUBLICATIONS

Liu, et al., "Effect of Non-Ionic Surfactants on the Formation of DNA/Emulsion Complexes and Emulsion-Mediated Gene Transfer", Pharmaceutical Research, vol. 13, No. 11, 1996, pp. 1642-1646.

Anderson, et al., "Polymerized Lyotropic Liquid Crystals As Contact Lens Materials", Physica A, 1991, 176, 151-167, Elsevier Science Publishers B.V. (North Holland).

Antonietti, et al., "Polymerization in Microemulsions-A New Approach To Ultrafine, Highly Functionalized Polymer Dispersion", Macromol.Chem.Phys., 1995, 196, 441-446, Hüthig & Wepf Verlag, Zug.

Antonietti, et al. "Morphology Variation Of Porous Polymer Gels By Polymerization in Lytropic Surfactant Phases, Macromolecules". 1999. 32, 1383-1389, American Chemical Society.

Antonietti, et al., "Polymer Gets With A Micron-sized, Layer-Like Architecture By Polymerization in Lyotropic Cocogem Phases", Langmuir, 1996, 14, 2670-2676, American Chemical Society.

Antonietti, et al., "Synthesis Of Sponge-Like Polymer Dispersions Via Polymerization Of Bicontinuous Microemulsions", Colloid Polym Sci, 1996, 274, 696-702, Steinkopff Verlag.

Antonietti, et al., "Microemulsions Polymerization: New Surfactant Systems By Counterion Variation", Adv. Mater., 1996, 8, 10, 840-844, VCH Verlagsgellshaft mbH, Weinheim.

Arenkov, et al., "Protein Microchips: Use For Immunoassay & Enzymatic Reactions", Analytical Biochemistry, 2000, 278, 123-131, Academic Press.

Bates, "Polymer-Polymer Phase Behavior", Science, Feb. 22, 1991, 25, 898-905.

Benedicto, et al., "Bicontinuous Cubic Morphologies In Block Copolymers & Amphiphile/Water Systems: Mathematical Description Through The Minimal Surfaces, Macromolecules", 1997, 30, 3395-3402, American Chemical Society.

Brinker, et al., *Sol-Gel Science*, 1990, Academic Press, San Diego.

Brown, "Dot & Slot Blotting of DNA, Current Protocols in Molecular Biology", 1993, Supplement 21, 2.9.15-2.10.16.

Burban, et al., "Organic Microporous Materials Made By Bicontinuous Microemulsion Polymerization", AIChE Journal, Apr. 1995, 41, 4, 907-914.

Chieng, et al., "Microporous Polymeric Materials By Microemulsion Polymerization: Effect of Surfactant Concentrations", Langmuir, 1995, 11, 3321-3326.

Chieng, et al., "Morphology Of Microporous Polymeric Materials By Polymerization Of Methyl Methacrylate & 2-Hydroxyethyl Methacrylate In Microemulsions", Polymer, 1995, 36, 10, 1941-1946, Elsevier Science Ltd, Great Britain.

Chieng, et al., "Formation Of Microporous Polymeric Materials By Microemulsion Polymerization Of Methyl Methacrylate & 2-Hydroxyethyl Methacrylate", Journal of Applied Polymer Science, 1996, 60, 1561-1568, John Wiley & Sons, Inc.

Hentze, et al, "Synthesis Of Organic Polymer Gets In Microemulsions & Lyotropic Mesophases", Ber.Bunsenges. Phys. Chem., 1997, 101, 11, 1699-1702, Wiley-VCH, Weinhelm.

Kempe, et al, "Receptor Binding Mimetics: A Novel Molecularly Imprinted Polymer", Tetrahedron Letters, 1995, 36, 20, 3563-3566.

Lee, et al., "Polymerization Of Nonlamellar Lipid Assemblies", J. Am. Chem. Soc., 1995, 117, 5573-5578.

Lindblom, et al. "Cubic Phases & Isotropic Structures Formed By Membrane Lipids-Possible Biological Relevance", Biochimica et Biophysica Acta, 1989, 988, 221-256, Elsevier Science Publishers B.V. (Biomedical Div).

O'Connell, et al, "Polyacrylamide Gets With Modified Cross-Linkages", Analytical Biochemistry, 1976, 76, 63-73, Academic Press, Inc.

Odian, *Principles of Polymerization*, 3rd Edition, (John Wiley & Sons: New York, New York), 1991, 232.

Paul, et al., "Cubic Phase Polymer Hydrogels: Templated Polymerization from Surfactant Mesophases", AIChE Meeting. Dallas, Texas, Oct. 31-Nov. 5, 1999, 71.

Peters, et al., "Rigid Macroporous Polymer Monoliths", Adv. Mater, 1999, 11, 14, 1169-1181, Wiley-VCH, Weinheim.

Raj, et al., "Formation of Porous Polymeric Structures By The Polymerization Of Single-Phase Microemulsions Formulated with Methyl Methacrylate & Acrylic Acid", Langmuir, 1991, 7, 2586-2591, American Chemical Society.

Raj, et al., "Polymerization Of Microstructured Aqueous Systems Formed Using Methyl Methacrylate & Potassium Undeconoate", Langmuir, 1992, 8, 1931-1936.

Raj, et al., "Synthesis Of Porous Polymeric Membranes By Polymerization Of Micro-emulsions", Polymer, 1993, 34, 15, 3305-3312, Butterworth-Heinemann Ltd.

Raj, et al., "Microcellular Polymeric Materials From Microemulsions: Control Of Microstructure & Morphology", Journal Of Applied Polymer Science, 1993, 47, 499-511, John Wiley & Sons, Inc.

Righetti, et al., "On The Limiting Pore Size Of Hydrophilic Gels For Electrophoresis & Isoelectric Focusing", Journal Of Biochemical & Biophysical Methods, 1981, 4, 347-363.

Righetti, et al., "Towards New Formulations For Polyacrylamide Matrices, As Investigated By Capillary Zone Electrophoresis", Journal Of Chromatography, 1993, 638, 165-176, Elsevier Science Publishers B.V.

Rill, et al., "Templated Pores In Hydrogels For Improved Size Selectivity In Gel Permeation Chromatography", Analytical Chemistry, Jul. 1, 1998, 70, 13, 2433-2438.

Samal, et al., "ElectroInitiated Polymerization Of Acrylamide In Acetonitrile Medium", J. Polym. Sci. Polym., 26, 1988, 1035-1049.

Sasthav, et al., "Characterization Of Microporous Polymeric Materials: Pore Continuity & Size Distribution Via Thermal Analysis", Journal Of Colloid & Interface Science, Sep. 1992, 152, 2, 376-385.

Seddon, "Structure Of The Inverted Hexagonal ($H_{II}$) Phase, & Non-Lamellar Phase Transitions Of Lipids", Biochimica et Biophysica Acta, 1990, 1031, 1-69, Elsevier Science Publishers BV (Biomedical Div).

Shiyakhtenko, et al., "Atomic Force Microscopy Imaging Of DNA Covalently Immobilized On A Functionalized Mica Substrate", Biophysical Journal , Jul. 1999, 77, 568-576, Biophysical Society.

Sosnowski et al., "Rapid Determination Of Single Base Mismatch Mutations In DNA Hybrids By Direct Electric Field Control", Proc. Natl. Acad. Sci. USA, Feb. 1997, 94, 1119-1123.

Srisiri, et al., "Polymerization Of The Inverted Hexagonal Phase", J. Am. Chem. Soc., 1997, 119, 4866-4873, American Chemical Society.

Svec, et al., "Molded Rigid Monolithic Porous Polymers: An Inexpensive, Efficient & Versatile Alternative To Beads For The Design Of Materials For Numerous Applications", Ind. Eng. Chem. Res., 1999, 38, 34-48, American Chemical Society.

Vasiliskov, et al., "Fabrication Of Microarray Of Gel-Immobilized Compounds On A Chip By Copolymerization", BioTechniques, Sep. 1999, 27, 3, 592-605.

Viklund, et al., "Monolithic, 'Molded', Porous Materials With High Flow Characteristics For Separations, Catalysis, Or Solid-Phase Chemistry: Control Of Porous Properties During Polymerization", Chem. Mater., 1996, 8, 744-750, American Chemical Society.

* cited by examiner

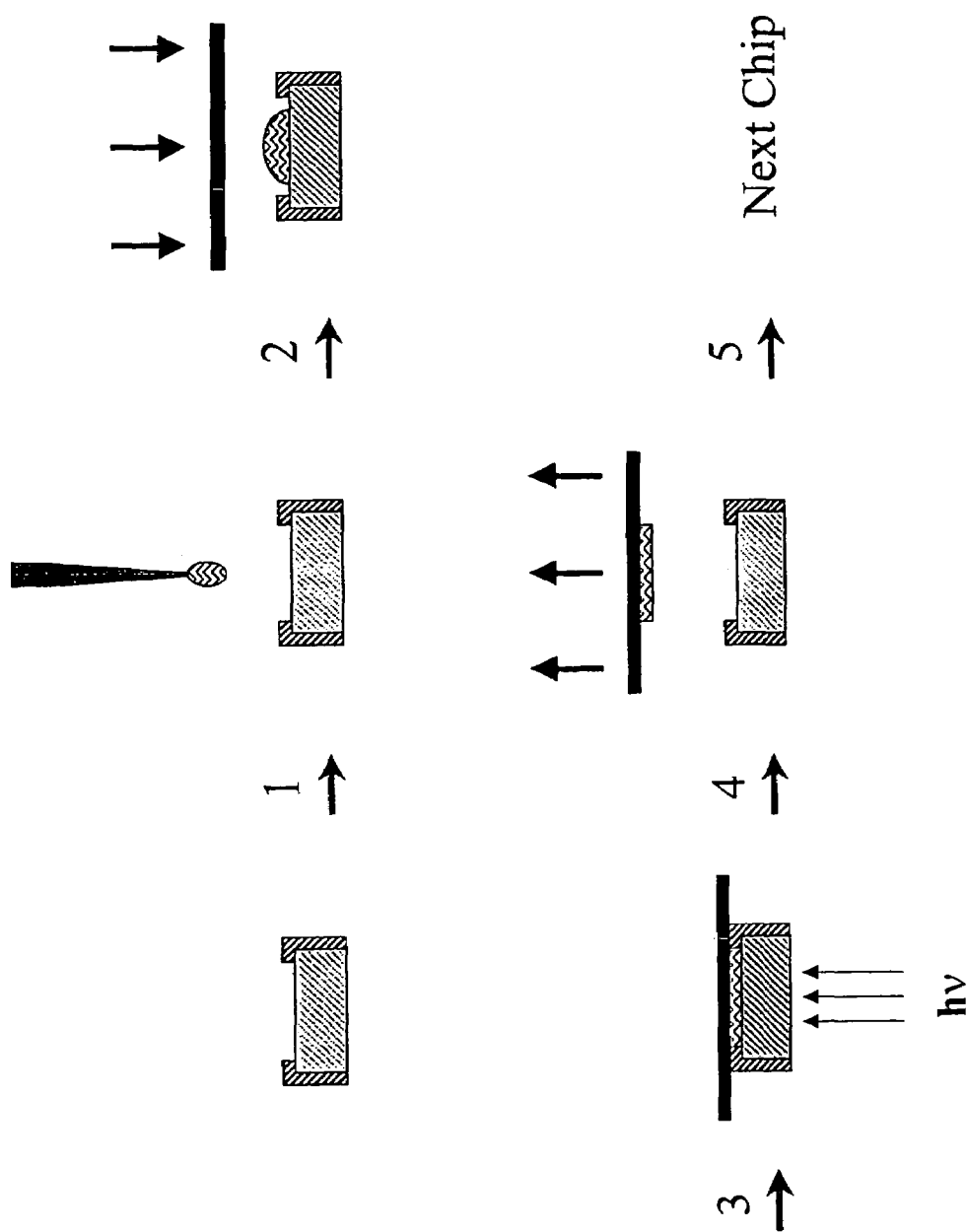

MESOPOROUS PERMEATION LAYERS FOR USE ON ACTIVE ELECTRONIC MATRIX DEVICES

This is a continuation of U.S. application Ser. No. 10/014,895, filed Dec. 10, 2001, which is expressly incorporated herein by reference in its entirety

FIELD OF INVENTION

The present invention provides improved synthetic polymer hydrogel permeation layers for use on active electronic matrix devices for biological assays. The permeation layers have a defined porous character, with mesopores in a size range between about 100 nanometers and about 1000 nanometers, and may also have micropores in the micrometer size range. The mesoporous synthetic hydrogel permeation layers demonstrate improved signal intensity and linearity characteristics as compared to nanoporous synthetic hydrogel permeation layers on active electronic matrix devices. In addition, the present invention also provides synthetic polymer hydrogel permeation layers which contain copolymerized attachment sites for nucleic acid probes or other biomolecules.

BACKGROUND

The following description provides a summary of information relevant to the present invention. It is not an admission that any of the information provided herein is prior art to the presently claimed invention, nor that any of the publications specifically or implicitly referenced are prior art to the invention.

By placing a plurality of nucleic acid probes on a surface, and exposing the surface to a sample containing target nucleic acids, many hybridization reactions may be carried out on a sample at the same time, simultaneously generating hybridization data for several target nucleic acids (the reverse dot-blot technique). Similarly, by immobilizing nucleic acids from several samples onto the surface, several samples may be probed with the same oligonucleotide probe at the same time (the dot-blot technique). Originally, dot-blot and reverse dot-blot hybridizations were carried out using nucleic acid probes crudely blotted onto a nucleic acid-binding membrane or filter. In the past two decades, several tools have been designed to place nucleic acid probes at defined locations in high densities on various types of surfaces (glass, polymers, silicon nitride, etc.) by methods such as physical deposition (e.g., ink-jet, microspray, pin deposition, microchannel deposition) or by in-situ polymerization techniques (e.g., photo-deprotection methods.) Such "microchip" based DNA arrays have been of great interest in recent years due to their enormous ability to facilitate rapid analysis of genetic information. Although very advanced techniques are utilized to generate these types of arrays, they still employ parallel hybridization of DNA to the immobilized capture probes in a passive mode. In other words, the nucleic acids present in the entire sample volume interact with the entire array surface at the same time, to the same extent.

In contrast, active electronic matrix arrays use an electric field to facilitate the rapid transport and hybridization of DNA on microchips. In general, active matrix array devices contain an array of electronically addressable microelectrodes on a substrate, which provide electric field control over a variety of biomolecular reactions including DNA transport, hybridization and denaturation. By using the electrodes to apply an electric field to a solution containing charged molecules, such as nucleic acids, the charge molecules can be rapidly transported to and concentrated at the electrodes which are biased opposite the charge of the molecules. This allows the transport of nucleic acid probes or amplicons to the microlocations in a very efficient and specific manner for binding to attachment moieties at the microlocations (a process sometimes referred to as "programming" the locations), allowing the generation of arrays for dot-blot or reverse dot-blot formats. After the probes or amplicons are immobilized at the microlocations, the electric field can again be used to rapidly direct the second hybridization assay component to the microlocation. Thus, electric field regulated hybridization is one to three orders of magnitude faster than passive hybridization under the same conditions, overcoming several of the limitations of passive hybridization.

These arrays, also known as active programmable electronic matrix devices, or APEX devices, have been extensively described, e.g. in U.S. Pat. Nos. 6,051,380 and 6,245,508, incorporated herein by reference in their entirety. In general, the devices comprise an array of individually controllable microelectrodes on a substrate, and optionally comprise additional counter electrodes for opposite biasing. The microelectrodes are overlaid by a thin permeation layer, defining the microlocations of the device above the microelectrodes. In addition to facilitating the attachment of biomolecules by providing a matrix to affix attachment moieties (e.g., streptavidin,) the permeation layer separates the biomolecules from the electrode surface where hydrolysis and other potentially detrimental electrochemical reactions can occur. Although the permeation layer retards or prohibits the movement of the biomolecules towards the microelectrode, the permeation layer is sufficiently permeable to small molecules to permit ion exchange between the electrode surface and the buffer medium, allowing an electric current to flow. The active electronic matrix chips usually use electric current and voltage conditions wherein electric current densities are at least $0.04$ $nA/\mu m^2$ (about 200 nA for an 80 µm diameter microlocation) and/or potentials sufficient to hydrolyze water. The electric current density is defined as the electric current divided by the area of the electrode used to support it.

Additionally, the effectiveness of the translocation of charged biomolecules such as nucleotide oligomers within an electronically-driven system such as an active electronic matrix chip depends on the generation of the proper gradient of positively and negatively charged electrochemical species by the anode and cathode, respectively. For example, effective nucleic acid (i.e. either DNA or RNA) transport may be accomplished by generation of protons and hydroxyl anions when the potential at the anode is greater than +1.29 V with respect to a 'saturated calomel electrode' (SCE). The transport efficiency of charged molecules increases with increasing current density, thus driving the desire for operation at higher voltage drops and current densities and, thus, the need for evermore robust permeation layers.

The application of an electric current through the permeation layer has also been found to produce considerable chemical and mechanical stress on the thin permeation layer coating at the electrode surface. It has been found that when such thin layers are applied onto electrodes without a covalent attachment to the electrode surface, the permeation layer is prone to separate or 'delaminate' from the electrode interface. It is believed this delamination is caused by a change in the chemical make-up at the interface between the permeation layer and the electrode resulting from the application of electronic potential at the electrode and by physical disruption from charged ions and gases emanating from the electrode. Thus, the permeation layer must have sufficient mechanical strength and be relatively chemically inert in order to withstand the rigors of changes at the electrode surface without inordinate stretching or decomposition.

Thus, the permeation layer of active electronic matrix devices is an important element in the overall function of the device. It must be sufficiently permeable to small aqueous ions, yet efficiently sequester biomolecules from the electrode surface. In addition, it must be able to withstand significant chemical and mechanical forces while maintaining its integrity and shape. Several materials have been utilized which provide these qualities. Agarose with glyoxal crosslinked streptavidin (SA) has been used as a permeation layer on commercially available, active electronic matrix chips, and the results of electronic hybridization of DNA on these chips has been reported in several publications (e.g., Sosnowski, et al., *Proc. Nat. Acad. Sci., USA*, 94:1119-1123 (1997), and Radtkey, et al., *Nucl. Acids Resrch.*, 28(7) e17 (2000.))

Agarose is a naturally sourced carbohydrate polymer hydrogel, containing long polymer strands which are crosslinked by non-covalent bonding. Such hydrogels are referred to as "physical hydrogels", as they derive their structure from non-covalent interactions, as compared to "chemical hydrogels", which derive their structure from covalent bonds (or cross-links) between the polymer strands. Agarose permeation layers provide good relative fluorescent intensity measurements in nucleic acid assays such as hybridization assays for single nucleotide polymorphisms (SNPs) and short tandem repeat sequences (STRs) in amplicon and capture-sandwich formats, and also in primer-extension type nucleic acid assays which have been used for gene-expression analysis.

However, some disadvantages are encountered in the use of agarose as a permeation layer material. Both the manufacturing process and the fact that agarose is a naturally-sourced product introduce some variation, which may vary performance from batch to batch, necessitating stricter quality controls. This is not ideal for large-scale manufacturing. Thus, an alternative material which is not naturally derived, which can be easily formed into a permeation layer on the device, and which will meet or exceed the operating standard of agarose, is greatly desirable.

Polyacrylamide and other synthetic polymer gels offer an alternative to agarose hydrogel permeation layers. These materials are wholly synthetic, and thus offer strict quality control of the components. In addition, they may be easily molded onto the microelectrode array surface with a high degree of uniformity across the entire device. Permeation layers which are between 1 and 2 µm thick in the dry state can be easily produced in this manner, and are amendable to high-throughput manufacture. After molding, streptavidin is covalently linked to the surface of the hydrogel to provide attachment sites for biotinylated oligonucleotide probes or amplicons. Although traditionally formulated polyacrylamide hydrogels made by the micromolding process are uniform, and offer better product control, they do not perform as well as the agarose streptavidin permeation layers in most nucleic acid assays. Thus, there is still a need for high-performance synthetic polymer hydrogel permeation layers for use on active electronic matrix chip devices.

SUMMARY OF THE INVENTION

Surprisingly, applicants discovered that synthetic polymer hydrogel permeation layers with defined porosity characteristics provide high-performance characteristics on active electronic matrix chip devices. Specifically, synthetic polymer hydrogels with mesopores of a size between nanometer-scale nanopores and micrometer-scale micropores performed as well as or better than the agarose physical hydrogel permeation layers in various nucleic acid assay formats. Thus, in a first aspect, the invention provides mesoporous synthetic polymer hydrogel permeation layers for use on active electronic matrix devices. In its most basic format, the assemblage of the permeation layer on the device comprises a mesoporous permeation layer overlying an individually addressable electrode on a substrate.

In some preferred embodiments of this aspect of the invention, the mesoporous synthetic polymer hydrogel permeation layers comprise pores that are between 100 and 1000 nm across. More preferably, the permeation layers comprise pores that are between 100 and 500 nm across, and most preferably, the permeation layers comprise pores that are between 200 and 500 nm across. As used herein to describe hydrogel pores, "across" is the longest linear dimension across the pore. For some applications, such as those using relatively longer nucleic acids (greater than about 70 nucleotides (hereinafter "nt") in length), primer extension-based assays, or other enzymatic reactions involving immobilized nucleic acids, it is preferred that the permeation layers also comprise micropores that are between 1.0 µm and 3.0 µm across, more preferably between 1.0 µm and 2.0 µm across. For mesoporous synthetic hydrogel permeation layer embodiments in which the permeation layer is less than 3 µm thick in the dry state, micropores are preferably between 1.0 µm and 1.5 µm across, in order to avoid exposure of the underlying electrode.

In other preferred embodiments of this aspect of the invention, the mesoporous synthetic hydrogel permeation layers have a porosity measurement θ of between about 2.0 and about 4.0, wherein θ is defined by the equation;

$$\theta \equiv \frac{\lambda - \lambda_0}{\lambda_S - \lambda_0} \approx \frac{\lambda}{\lambda_S}$$

wherein integrated light intensity readings λ are taken using dark field microscopy of a dry hydrogel layer on the test chip (λ), a standard layer ($\lambda_S$) with a medium degree of phase separation and a non-phase separated, or solid, layer ($\lambda_0$) on a Leica darkfield compound optical microscope, and wherein the standard layer is a polyacrylamide hydrogel standard composition (composition S):

Acrylamide: Bisacrylamide 19:1 (mol/mol)
Total monomer content 20% by weight

The standard layer and the test layer are similarly prepared and molded (or, optionally, placed) onto the substrate. For the θ measurement, both the standard permeation layer and the test permeation layer are about 1.7 µm thick in the dry state. Under the illumination conditions used in the examples, $\lambda_S$ for the standard composition was 60±1.5. More preferably, the mesoporous synthetic hydrogel permeation layers have a θ between about 2.0 and about 3.8. For applications using relatively short nucleic acids, less than or equal to about 70 nt in length, mesoporous synthetic hydrogel permeation layers with a θ between about 2.0 and about 3.0 are more preferred. For applications using relatively longer nucleic acids, greater than about 70 nt in length, primer extension-based assays, or other enzymatic reactions involving immobilized nucleic acids, mesoporous synthetic hydrogel permeation layers with a θ between about 3.0 and about 3.8 are preferred.

Preferred mesoporous synthetic hydrogel permeation layers of the invention comprise an acryloyl or acrylamido based synthetic polymer hydrogel, more preferably an acrylamide based synthetic polymer hydrogel, and also more preferably a methacrylamide based synthetic polymer hydrogel. Preferred mesoporous synthetic hydrogel permeation layers of the invention are also covalently anchored to the underlying electrode(s) and/or substrate. In addition, more preferred embodiments of the mesoporous synthetic hydrogel permeation layers of the invention comprise copolymerized attachment moieties for the attachment of derivatized biomolecules as specific binding entities (e.g., nucleic acids, proteins, etc.). In preferred embodiments, these copolymerized attachment moieties have the general formula:

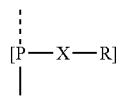

wherein,

P is a polymerizable moiety covalently attached to one or two moieties selected from the group consisting of: a monomeric unit of the synthetic polymer and another P—X—R group, as defined herein, wherein the other P—X—R group may be the same as or different from the first P—X—R group, further wherein the dashed line is a covalent bond to the second moiety if P is covalently attached to two moieties;

X is a covalent bond or a linking moiety; and

R is a functional moiety for attaching, either covalently or non-covalently, a biomolecule.

In more preferred embodiments, P is an acryloyl or acrylamido moiety, more preferably an acrylamide moiety. Also, in more preferred embodiments, R is biotin or a biotin binding moiety, such as, for example, streptavidin or avidin. In other more preferred embodiments, R is a reactive moiety for use in amine, hydrazine, or hydrazide attachment chemistries. Some preferred R include an active N-hydroxyl succinimidyl (NHS) ester, a sulfonated NHS ester, an aldehyde, an acid, an acyl halide, a thiol, a disulfide, an amine, an ether, an ester, a thioether, a thioester, a hydrazine, or a hydrazide. In some more preferred embodiments R is a succinimidyl ester. In another group of preferred embodiments R is an aldehyde. In yet another group of preferred embodiments, R is a hydrazide. In other preferred embodiments, R is a psoralen.

As the use of copolymerized attachment moieties has proven advantageous in order to provide a greater density of attachment moieties for the attachment of specific binding entities (such as nucleic acids or proteins) to synthetic polymer hydrogel permeation layers for active electronic matrix chip devices, the synthetic polymer hydrogel permeation layers with copolymerized attachment moieties of any porosity are another aspect of the present invention. These permeation layers overlie at least one electrode on a substrate, and comprise copolymerized attachment moieties of the general formula:

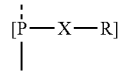

as defined above.

In more preferred embodiments, P is an acryloyl or acrylamido moiety, more preferably an acrylamide moiety. Also, in some preferred embodiments, R is a reactive moiety for use in amine, hydrazine, or hydrazide attachment chemistries, such as an active N-hydroxyl succinimidyl (NHS) ester, a sulfonated NHS ester, an aldehyde, an acid, or the like. In other preferred embodiments, R is a moiety capable of participating in a biotin-binding pair reaction, i.e., either a biotin-moiety or a biotin-binding moiety. Thus, these preferred R moieties in the present invention bind to derivatized biomolecules, which have been derivatized to contain either a biotin-moiety or a biotin-binding moiety (e.g., streptavidin). As many biomolecules may be readily derivatized with biotin or a biotin analog, in preferred embodiments of the invention R is a biotin-binding moiety such as, for example, streptavidin, avidin, or chemical or recombinantly engineered derivatives thereof. As will be appreciated by those of skill in the art, the attachment molecule may contain more than one P moiety attached to an R moiety, especially in the case of proteinaceous multi-subunit R moieties such as streptavidin. In some preferred embodiments of the invention, the attachment molecule has about one P moiety for each biotin-binding site on R. In other preferred embodiments of the invention, the attachment molecule has about one P moiety for each R. Preferred X may include a covalent bond, as well as commonly utilized hydrophilic linker molecules such as polyethylene glycols (PEGs), which may be connected to R and P by common linkage chemistries such as ester, amide, ether or other common linkage chemistries. Linkage chemistries which are more stable over a wide pH range, such as amide linkages, are preferred.

In preferred embodiments of the permeation layer aspects of the invention, the permeation layer is anchored by a covalent linkage to the electrode, to the substrate, or to the electrode and the substrate. In these embodiments, silane-based linkers comprising a copolymerizable moiety are preferably utilized to covalently anchor the permeation layer.

Generally, in preferred embodiments of the permeation layers of the invention, the permeation layers are between about 0.5 μm and about 10 μm thick in the dry state, more preferably between about 1.0 μm and about 5.0 μm thick in the dry state, and most preferably between about 1.0 μm and about 2.0 μm thick in the dry state [or at least about 8-9 μm thick when in equilibrium with aqueous buffer]. Also, in preferred embodiments, the permeation layers vary in thickness across the electrode array of the active electronic matrix chip device by less than 0.5 μm, more preferably by less than 0.2 μm, and most preferably by less than 0.1 μm, as measured in the dry state.

In another aspect, the present invention provides methods for the production of mesoporous synthetic hydrogel permeation layers on active electronic matrix chip devises by in-situ polymerization. These methods generally comprise:

placing an appropriate volume of a polymerization mixture comprising polymerizable monomers, a cross-linking agent, and a porogen into a mold cavity of a micromold, wherein the mold cavity comprises a bottom and at least one side;

contacting a substrate, comprising a plurality of electrodes on the substrate, with the mold to form a closed volume of the polymerization mixture, wherein the closed volume is in contact with at least one of the electrodes on the substrate;

polymerizing the polymerization mixture; and removing the micromold, to reveal the polymerized mesostructured synthetic hydrogel permeation layer overlying at least one electrode on the substrate. In preferred embodiments, the porogen is a templating porogen, such as, e.g., a micelle forming porogen, a solid templating porogen, or a liquid templating porogen. More preferably, the templating porogen is a micelle forming surfactant, most preferably a nonionic or zwitterionic surfactant comprising an aliphatic carbon chain and a polyether, such as Brij surfactants. In embodiments where a templating porogen is utilized, the method of the invention preferably comprises an additional step of selectively removing the templating porogen with a solvent. In a more preferred embodiment, the template forming porogen is a micelle forming surfactant, and the method further comprises selective removing the surfactant with water.

In preferred embodiments of the method of producing mesoporous synthetic hydrogel permeation layers, the polymerization mixture comprises acryloyl or acrylamido monomers, most preferably an acrylamide monomer such as methacrylamide. Additionally, in preferred embodiments, the polymerization mixture comprises a polymerizable cross-linker (for example, methylene bisacrylamide when the monomer is an acrylamide). In preferred embodiments, the polymerization mixture comprises a polymerization free-radical initiator. In more preferred embodiments, the free-radical initiator is a photoinitiator, the micromold bottom is transparent to a radiation of a wavelength which activates the photoinitiator, and the polymerization step comprises irradiating the mold with radiation of the wavelength appropriate to activate the photoinitiator.

In other aspects of the present invention, the mesoporous synthetic hydrogel permeation layer active electronic matrix device of the invention is electronically addressed with derivatized biomolecules to produce an addressed mesoporous synthetic hydrogel permeation layer device with specific binding entities attached at one or more microlocation of the devices. In some preferred embodiments, the biomolecules are nucleic acids, e.g., nucleic acid probes or sample nucleic acids. In other preferred embodiments the biomolecules are peptides, polypeptides, or proteins (such as antibodies).

In other aspects of the present invention, the mesoporous synthetic hydrogel permeation layer device of the invention is used in a nucleic acid based assay or reaction. Exemplary assay and reaction formats include, but are not limited to: hybridization assay formats (for example, dot blot assay formats, reverse dot-blot assay formats, nucleic acid sandwich assay formats, base-stacking stabilized hybridization assay formats) with or without electronic stringency and/or electronic washing, primer extension reporting assays (for example, gene expression analysis with primer extension reporting), immobilized nucleic acid amplification reactions (for example, strand displacement amplification, ligation-dependent strand displacement amplification, polymerase chain reaction amplification, transcription mediated amplification or nucleic acid sequence based amplification, rolling circle amplification), ligation reactions, and nucleic acid cleavage reactions (for example, restriction endonuclease reactions, endonuclease reactions, and exonuclease reactions.) In addition, the mesoporous synthetic polymer hydrogel permeation layer devices of the invention may used in nucleic acid or polypeptide synthesis applications, as has been described for APEX devices.

In additional aspects of the present invention, the mesoporous synthetic hydrogel permeation layer device of the invention is used in an immunochemistry based assay. Exemplary assay formats include, but are not limited to: addressing the microlocations of the device with antigens (e.g., peptides, proteins, carbohydrates, lipids, proteoglycans, glycoproteins, etc.) in order to assay for antibodies in a bodily fluid sample by sandwich assay, competitive assay, or other formats; and addressing the microlocations of the device with antibodies, in order to detect antigens in a sample by sandwich assay, competitive assay, or other assay formats.

BRIEF DESCRIPTION OF THE DRAWINGS

FIG. 15: A schematic drawing of the micromolding process. Starting with a micromold with a bottom transparent to a light wavelength (hv), a drop of polymerization mixture is placed into the mold in step 1. In step 2, the active electronic matrix chip substrate is brought into contact with the mixture and the mold, forming a closed volume of the polymerization mixture. In step 3, the mixture is polymerized by irradiating the mold with a light wavelength appropriate to initiate polymerization. In step 4, the substrate is removed, along with the newly formed permeation layer over the electrodes, allowing the process to start over again with a new active electronic matrix chip substrate in step 5.

DETAILED DESCRIPTION OF THE INVENTION

Figure 1:
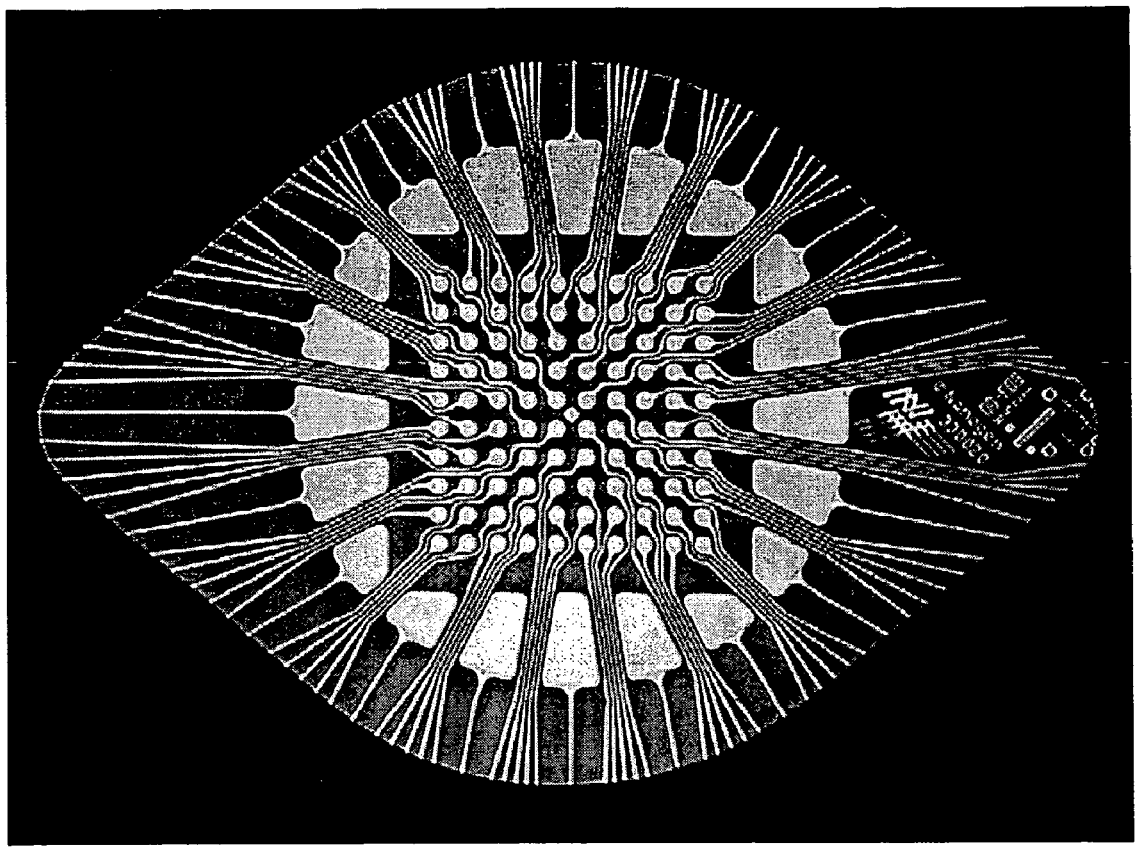
FIG. 1: A photograph of the electronics of a NanoChip® 100 site device, having electrodes with an electrode diameter of 80 μm and center to center spacing of 200 μm. The individually controllable electrodes define the active sites of the device. The electrodes shown are a layer of platinum (a non-reactive noble metal] formed upon a layer of titanium/tungsten, which is formed upon a layer of a silicon dioxide substrate. Note that the conductive layer of electrodes is overlaid with a layer of insulating silicon dioxide, which is etched away to reveal the electrode pads. Also note the ring of counter electrodes surrounding the central 10 by 10 array, which can be oppositely biased to allow use of all of the microlocation electrodes in a (+) or (−) bias state.

As has been described, a key role in the function of active electronic matrix devices is played by the ion-permeable permeation layer which overlies the electrodes of the microlocations, or active sites, of these devices. As part of its function, the permeation layer provides attachment moieties for the attachment and immobilization of nucleic acids (or other specific binding entities, such as antibodies, or synthetic binding moieties such as pyranosyl-RNA). More importantly, the permeation layer separates the attached or tethered oligonucleotides and hybridized target DNA sequences from the highly reactive electrochemical environment generated immediately at the electrode surface. This highly reactive electrode surface, and the electrochemical products concentrated at the electrode surface, can rapidly destroy DNA probes and target DNA sequences which contact the surface or approach it too closely. Similar detrimental effects may be encountered with other macromolecular binding entities immobilized directly on the electrode surface. The permeation layer allows oligonucleotides and DNA fragments to be electronically concentrated above, rather than on, the electrode surface and hybridized to anchored complementary oligonucleotides while being protected from the reactive electrode surface and its immediate environment. The permeation layer also allows the gradual diffusion of the electrochemical reaction products ($H^+$, $OH^-$, gasses, etc.) into the solution around the microlocation, allowing these products to balance the charge through the permeation layer by ion exchange and to react with buffer species. Thus, the design of the microelectrode and permeation layer, forming a microlocation structure, allows high current densities to be achieved in a very confined area, while minimizing the adverse effects produced by the electrode itself.

Once specific binding entities, such as nucleic acids, have been addressed to microlocations and immobilized, the addressed devices are able to control and actively carry out a variety of assays and reactions. Analytes or reactants can be transported by free field electrophoresis to any specific microlocation where the analytes or reactants are effectively concentrated and reacted with the specific binding entity at the microlocation. The sensitivity for detecting a specific analyte or reactant in dilute sample solutions is improved because of this concentrating effect. An additional advantage, which also improved the specificity of the assays carried out on the device, is that any un-bound analytes or reactants can be removed by reversing the polarity of a microlocation (also known as "electronic washing".)

The ability to produce a precisely controlled high current level, or density, at individual microlocations even allows the selective "de-hybridization" of DNA fragments, achieving hybridization selectivity at the level of single base mismatches. Thus, the devices can further improve the specificity of assays and reactions by providing another parameter to encourage mismatch de-hybridization (along with the more traditional parameters of temperature and chemical environment), which is known as "electronic stringency", or "electronic stringency control (ESC)." For DNA hybridization reactions which require different stringency conditions, ESC overcomes an inherent limitation of conventional array technologies, which must rely on stringency conditions which are consistent for all sites over the entire array. The active devices of this invention can electronically produce different stringency conditions at each microlocation. This adds another controllable factor affecting hybridization, along with the more traditional factors such as temperature, salt concentration and the presence of chaotropic agents. Thus, all hybridizations can be carried out optimally in the same bulk solution, and multiple hybridization reactions can be carried out with minimal outside physical manipulations. Additionally, it may be unnecessary to change temperature in some cases, and the need for multiple washing procedures is greatly reduced.

Thus, the permeation layer of active electronic matrix devices is more than simply a mechanical support to hold attachment sites for specific binding entities. It is also an important factor in the overall performance and efficiency of the devices in their active electronic modes. Unlike coatings or gel supports which have been described for passive array devices, e.g., the gel-block arrays described in U.S. Pat. No. 5,770,721, which simply use hydrogel matrices as an attachment scaffold, permeation layers used on the active electronic matrix devices described herein must also allow the efficient active electronic transport of biomolecules to the microlocations of the device, and be conducive to electronic hybridization and/or stringency procedures.

As noted above, agarose hydrogels containing glyoxalcrosslinked streptavidin have proven to be effective permeation layer materials on active electronic matrix chip devices. In general, these permeation layer formulations have provided good mean fluorescence indices with minimal background. SNP assays run on the SA-agarose chips have demonstrated nearly 100% accuracy in several tests run with actual genomic samples, together with a high discrimination ratio for discerning between alleles in both homozygous and heterozygous samples. In addition, very good results have been obtained using SA-agarose active electronic matrix chips in STR and gene expression analysis assays.

However, as also described above, the use of SA-agarose as a permeation layer has several disadvantages in the manufacturing context. Agarose is a physical hydrogel, which derives its semi-solid structure from non-covalent interactions between long polysaccharide chains. As these interactions are temperature-dependent, changes in temperature change the viscosity of the agarose solution: at higher temperatures, the solution is more liquid, while it forms a solidified gel at room temperature. Thus, in order to coat the agarose permeation layer onto the active electronic matrix chip electrode array, the agarose solution must be kept at a relatively high and constant temperature during the manufacturing process. This also must be balanced with maintaining the activity of the streptavidin crosslinked to the agarose in the solution, which can denature if the temperature is too high. The current manufacturing method is to spin-coat the agarose solution onto the active electronic matrix chip surface. Thus, the agarose permeation layer production methods add significantly to the resources expended in producing the device.

Although this produces a fairly uniform thickness, submicron variations in thickness are often encountered when comparing the thickness of the permeation layer over microlocations on different sites on the chip. In addition, because agarose is a natural product, batch to batch variability may be seen with regard to its chemical characteristics and its performance as a permeation layer. This variability in both the materials and the manufacturing methods decreases the number of active electronic matrix chips which will meet quality control standards, also increasing the resources necessary to produce high-quality active electronic matrix chips with agarose-based permeation layers.

In contrast to the naturally-sourced physical hydrogels, such as agarose, synthetic polymer chemical hydrogels offer a more easily controlled quality and production characteristics. Synthetic polymer hydrogels are produced from individual monomeric components, which are usually synthesized themselves from basic organic chemical components. The monomers can be purified to very high quality, with identical physical and chemical characteristics between production batches. The monomeric components can be mixed in various formulas with cross-linker moieties and polymerized by a triggered initiator (e.g., by exposure of a photoinitiator to UV). Thus, chemical hydrogels offer strict control over the rate of polymerization and the characteristics of the resulting hydrogel, as compared the control afforded by physical hydrogels formed by pre-polymerized chains.

In addition, synthetic polymer hydrogels offer many advantages for mass production. They be easily molded onto the microelectrode array surface in situ with a high degree of uniformity across the entire device. Microreaction molds and methods of using them to form thin, uniform, synthetic polymer hydrogel layers on the surface of active electronic matrix chips have been described in WO 01/43938, Havens et al, incorporated herein by reference in its entirety. The microreaction molds disclosed comprise a mold cavity, with at least one side transparent to an electromagnetic radiation wavelength. In these systems, a small volume of the polymerization mixture (monomers, cross-linkers, and photoactivator) is placed into the mold cavity. The microelectrode array substrate is then pressed against the mold, forming an enclosed volume of the polymerization mixture on the substrate. The polymerization reaction is initiated by irradiating the enclosed volume with an appropriate wavelength of light for the photoinitiator (e.g., UV), and the polymerization reaction is allowed to proceed to completion. When the mold is removed, a thin, uniform, synthetic polymer hydrogel permeation layer has been formed on the microelectrode array.

Permeation layers which are between 1 and 2 μm thick, with sub-micron variations in thickness, can be easily produced in this manner, and are amendable to high-throughput manufacture. Multi-layer permeation layers (either overlaid or graft-polymerized onto the prior layers) be made in this manner as well, by using a series of molds with differing depths and/or widths. In addition, the molds can be designed to form individual permeation layers over each individual microelectrode, creating individually formed microlocations. In this manner, it is even possible to vary the permeation layer composition from microlocation to microlocation over the array of the active electronic matrix chip.

Given the advantages of using synthetic polymer hydrogel permeation layers, various synthetic polymer hydrogel formulations were tested for use as permeation layer materials. Initially, polyacrylamide gels which were surface derivatized with SA were tested. However, the standard nanoporous polyacrylamide formulations used did not produce permeation layers which provided fluorescent intensity, signal linearity, and other performance characteristics which were comparable to those obtained using agarose-SA physical hydrogel permeation layers. Thus, alternative formulations were explored which would alter the physical characteristics of the polyacrylamide chemical hydrogel matrix.

Figure 2:
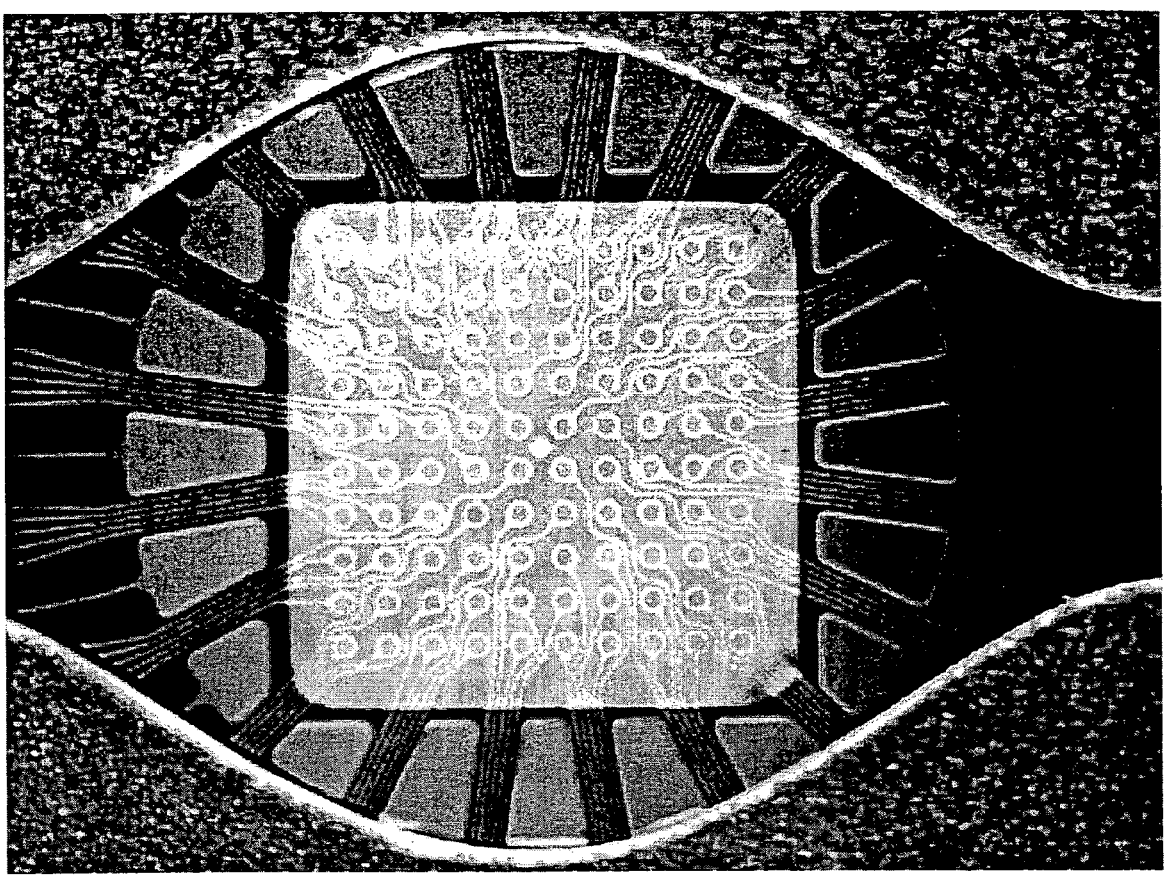
FIG. 2: A stereomicroscope dark-field photograph of the same type of device, with a mesoporous permeation layer. The permeation layer was micro-molded onto the device.
Figure 9:
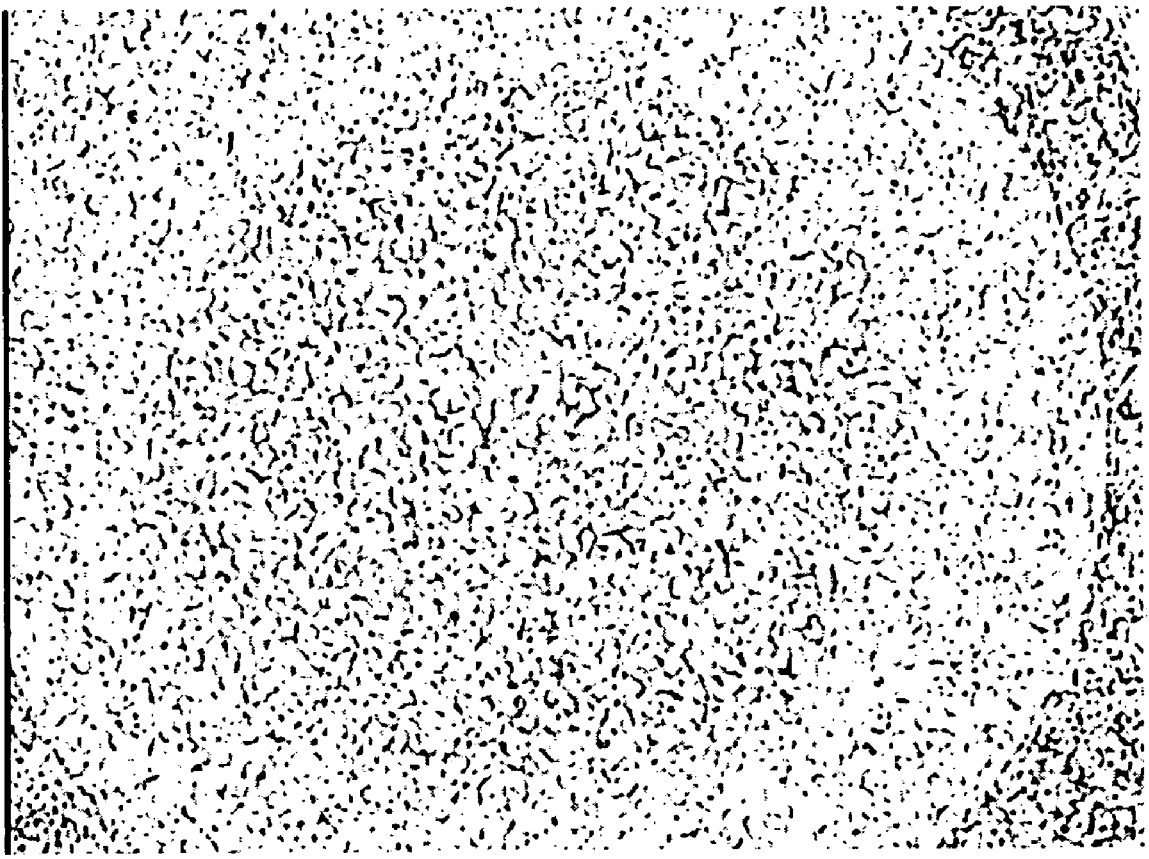
FIG. 9: A darkfield compound microscope photograph (Leica iNM 100 with an Optromics™ video camera) of a single microlocation, or pad, of a device, like those used to determine the light scattering values for the θ calculation. The pad diameter is 80 μm.

Surprisingly, it was discovered that polyacrylamide synthetic polymer hydrogel permeation layers with defined porosity characteristics performed dramatically better in all of the nucleic acid assay formats tested, as compared to synthetic polymer hydrogel permeation layers with pore sizes smaller than the defined range. These permeation layers possess pores in a middle size range: between about 100 and about 1000 nm across. Thus, these synthetic polymer hydrogel permeation layers have been designated "mesoporous," as opposed to possessing nanometer-scale pores ("nanoporous"), or micrometer-scale pores ("microporous"). Mesoporous synthetic hydrogel permeation layers also show a macroscopic difference from nanoporous permeation layers, as shown in FIG. 2. Instead of a clear gel, mesoporous synthetic hydrogel permeation layers appear milky or translucent, due to the scattering of light through the layer caused by the separation of the gel and solution phases. This light-scattering effect, also shown in the dark field micrograph in FIG. 9, forms the basis for the porosity measurement θ, discussed below and in Example 3.

The characteristics of increased porosity in synthetic polymer hydrogel formulations were further characterized using a template-type porogen to introduce various degrees of porosity, or phase separation, into the synthetic polymer hydrogels. As the hydrogel comprises a meshwork of polymer strands in the aqueous solution, it can be thought of as a two-phase system: the meshwork, or solid phase, and the surrounding solution phase. When the meshwork is separated to create pores (or areas where the meshwork is not), then the phases become more separate, creating larger and more distinct pore/void areas. By using a micelle-producing surfactant, Brij 700, the degree of phase separation could be controlled by varying the concentration of the surfactant in the polymerization solution, thus varying the prevalence and average size of the micelles.

As described in Example 1, four permeation layer formulations, with different degrees of phase separation, were used to produce active electronic matrix chip devices which were the subject of the majority of experiments: 4012-1, with 0 mg/ml Brij 700 [No porogen—a basic acrylamide/bisacrylamide chemical hydrogel with copolymerized streptavidin attachment moieties]; 4012-2, with 11 mg/ml Brij 700; 4012-3, with 18 mg/ml Brij 700; and 4006-1, mg/ml Brij 700. 4012-2, 4012-3, and 4006-1 are all considered to be mesoporous synthetic polymer hydrogel permeation layers. Electron micrographs (FIGS. 5 A & B, 6 A & B, 7 A & B, and 8 A & B) were taken of the permeation layers, prepared as described in Example 2. As can be clearly seen from the 45,000× and 50,000×scans of the permeation layers, 4012-1 appears to be relatively smooth, with pores in the nanometer range. In contrast the other three formulations have a fairly consistent fine morphology at this magnification, showing mesopores between about 100 and about 500 nm across. In addition, in the 5,000×scans, 4012-3 and 4006-1 also exhibit a microporous morphology, with pores between about 1 μm and about 2 μm across.

Figure 3:
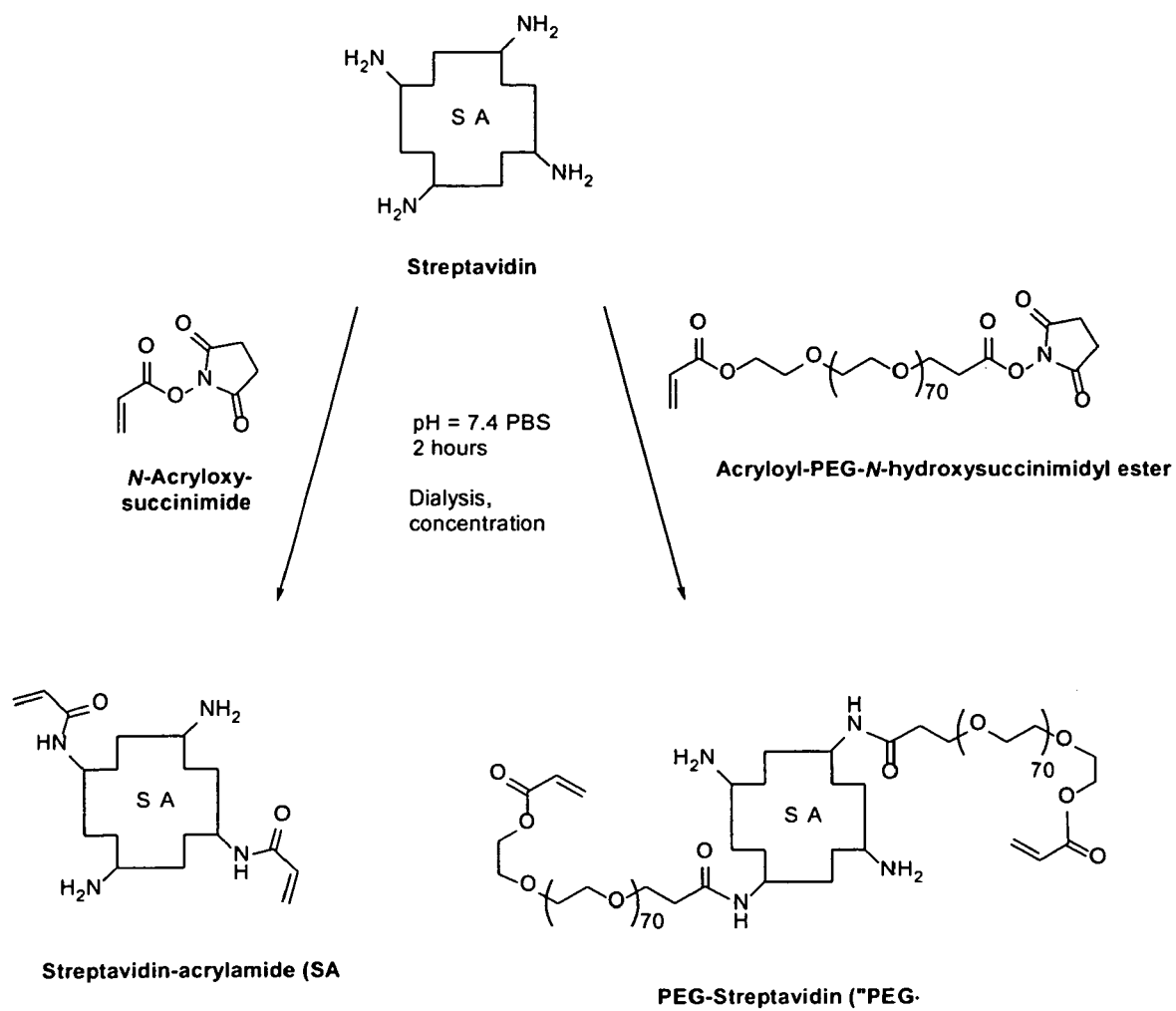
FIG. 3: A reaction scheme showing the formation of two derivatized streptavidin (SA) proteins for co-polymerization with acrylamide hydrogels. Reaction of SA with N-acryloxysuccinimide yields acrylamide groups, while the reaction of SA with the acryloyl-PEG-N-hydroxysuccinimidyl ester yields a SA with PEG-ester linked acrylate moieities. Ester-linked SA derivatives are less preferred for use in hydrogel formulations because of their decreased stability over a wider range of pH. Similarly, attachment chemistries are not base- or acid- labile are generally more preferred, but not necessary, for use in the synthetic polymer hydrogels of the permeation layer formulations. For instance, N-acryloxysuccinimide may be used as an attachment group for copolymerization if amine, hydrazide, or similar chemistries are to be used to covalently attach, e.g., a nucleic acid probe or amplicon to the permeation layer of the device.
Figure 10:
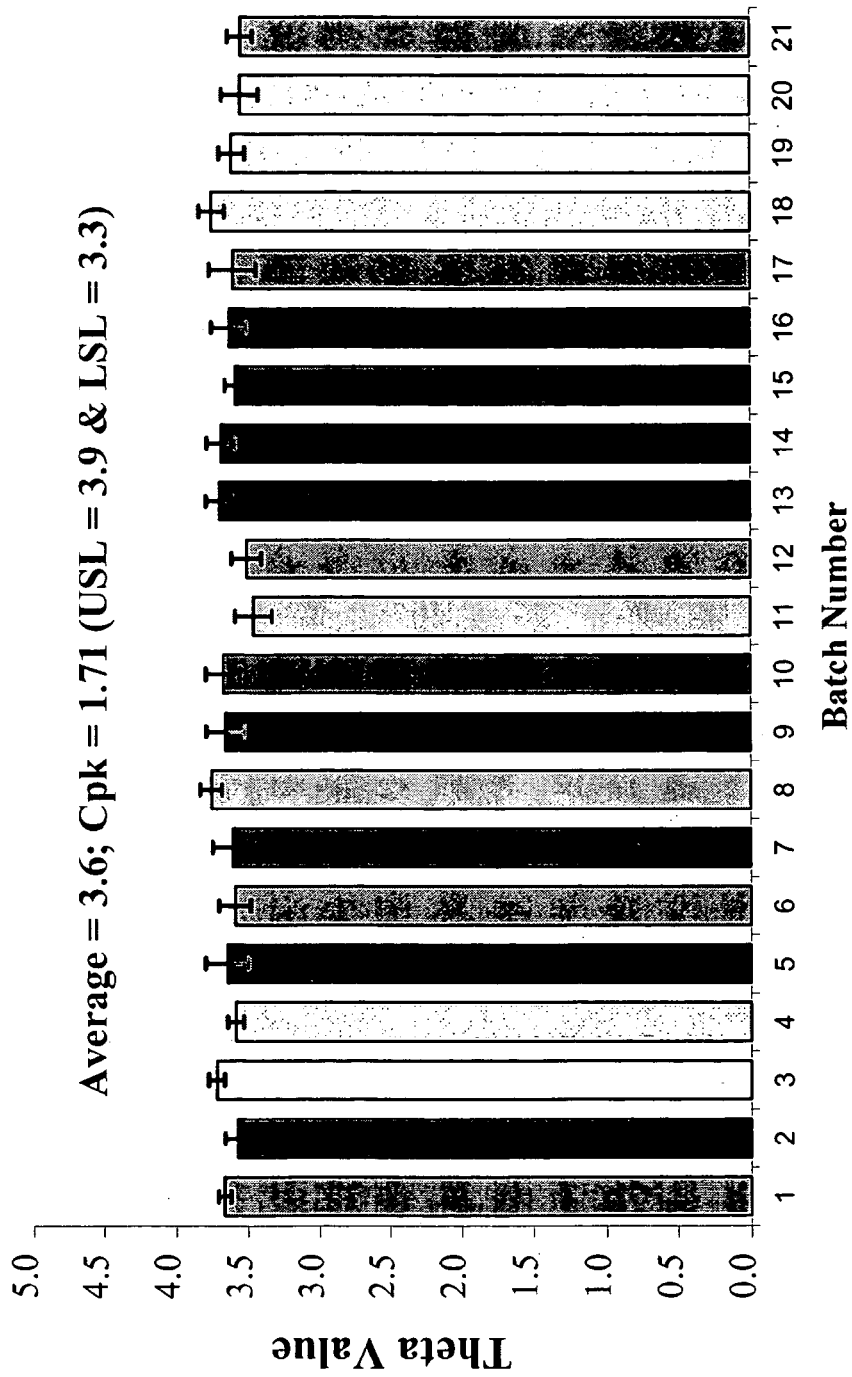
FIG. 10: A chart showing θ measurements for several batches of 4006-1 permeation layers formed on NanoChip® devices. The θ porosity measurement is very consistent over twenty different batches (mean 3.63 θ, std±0.07 θ). These data show that mesoporous synthetic hydrogel permeation layers can be consistently molded onto active electronic matrix devices. Likewise, the consistency of the light-scattering measurement technique is also validated.
Figure 14:
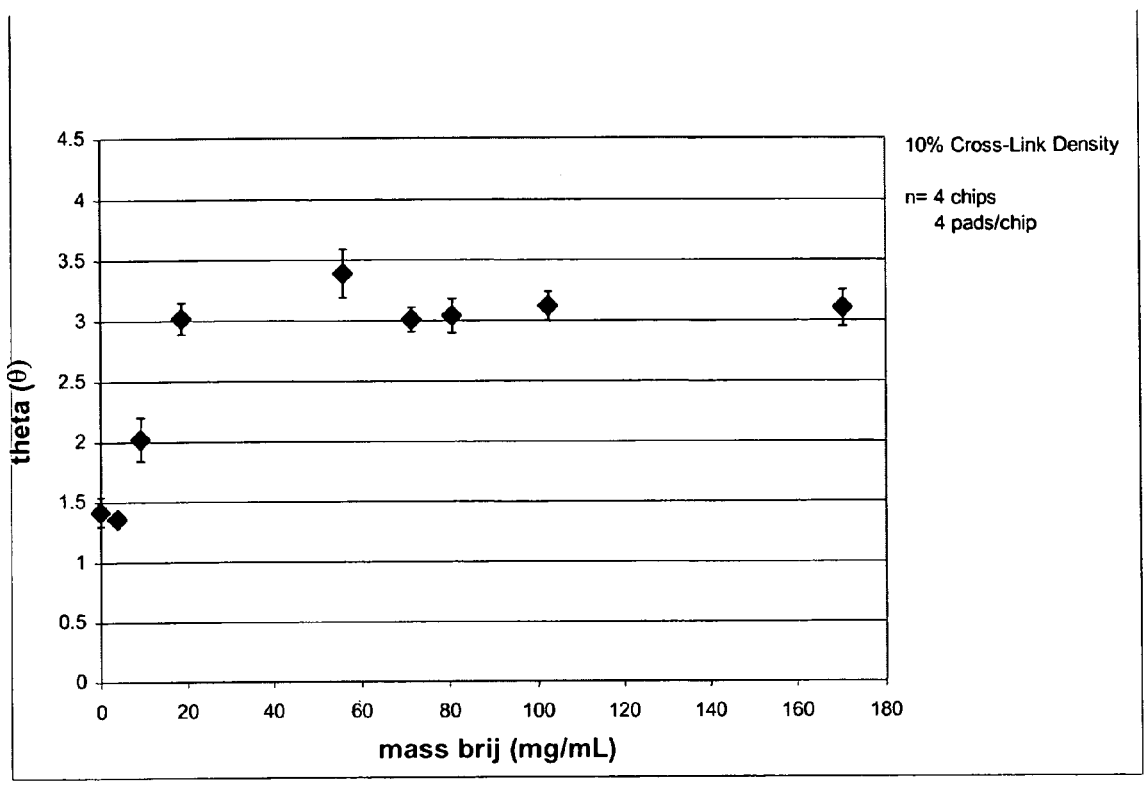
FIG. 14: A chart showing θ measurements for synthetic polymer hydrogel permeation layers made by using various amounts of Brij 700 surfactant as a template porogen.

In order to more easily quantify the porosity characteristics of the permeation layer formulations, the measurement θ was devised, as described in Example 3, based on light-scattering analysis under dark field microscopy. The standard layer is a polyacrylamide hydrogel standard composition (composition S):
  Acrylamide: Bisacrylamide 19:1 (mol/mol)
  Total monomer content 20% by weight
  Under the illumination conditions used in the examples, $\lambda_s$ for the standard composition was 60±1.5. By comparison to the standard composition S, the relative phase separation, and thus porosity, of the synthetic polymer hydrogel permeation layers can be quantified. The θ of 4012-1 was 1.5, while the θ's of the mesoporous permeation layers were between 3.0 and 3.5. In order to more thoroughly characterize the effect of different concentrations of Brij surfactant on the porosity measurement θ, eight permeation layers based on the 4012-1 formulation, with varying concentrations of Brij 700 surfactant from 3.9 to 170.4 mg/ml, as described in Example 7, were compared to the 4012-1 formulation. The θ values for these synthetic polymer hydrogel permeation layers are shown in FIG. 14. As can be seen in the Figure, the porosity of the permeation layers changes rapidly between the 9.3 mg/ml formulation (slightly less than 4012-2) with a θ of 2, and the 18.6 mg/ml formulation (slightly more than 4012-3) with a theta of about 3. This suggests a critical phase separation change for the use of the Brij surfactant template porogen at around 10 mg/ml: above this concentration, the θ values hover in the 3.0 to 3.5 range. Although applicants are not bound by any particular theory, one possibility is that the Brij micelles aggregate at the higher concentrations. This could explain the appearance of micropores in the 4012-3 electron micrographs. Interestingly, the use of a different streptavidin moiety for copolymerization produced increased porosity, as measured by θ, as described in Example 3. As seen in FIG. 10, batches of permeation layers with the same formulation as 4006-1, except for the substitution of amide-linked acrylamido SA for ester-PEG linked acryloyl SA (see FIG. 3 for comparison) produced mesoporous synthetic hydrogel permeation layers with θ's averaging about 3.6. Thus, the porosity of the mesoporous synthetic hydrogel permeation layers may be influenced by a combination of factors, including the presence of porogens, the type of copolymerized attachment moiety used, and more conventional parameters such as cross-linker ratio and total monomer concentration.

Figure 12:
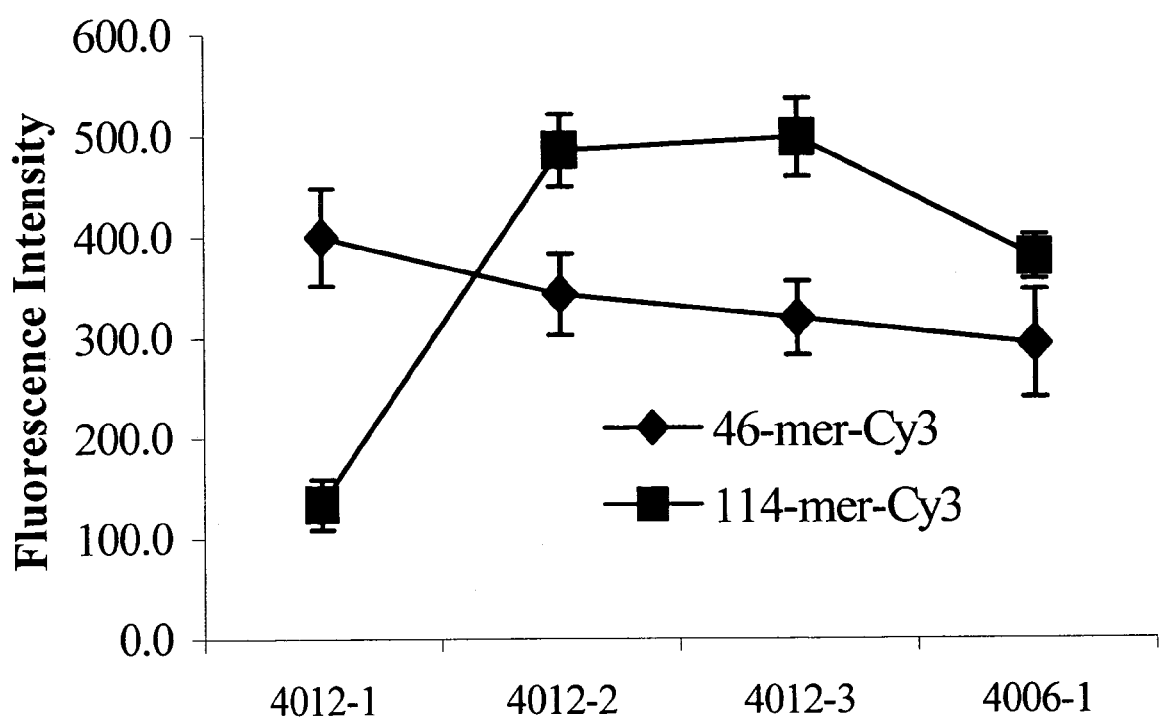
FIG. 12: A chart showing MFI readings from the two nucleic acid immobilization experiments described in Example 5. The 46 nt oligomers immobilization experiment results are indicated by diamonds (♦), and the 114 nt amplicon immobilization experiment results are indicated by squares (■). Note that the relative binding efficiency of the larger nucleic acid increases significantly with increased porosity, while the binding efficiency of the small nucleic acid decreases very slightly with increased porosity.

In several nucleic acid assays using electronic addressing and hybridization techniques, these permeation layers showed distinct differences in function. As described in Example 5, and shown in FIG. 12, the ability of a relatively large polynucleotide (114-mer) to be immobilized by a biotin-streptavidin interaction in the mesoporous synthetic hydrogel permeation layers was increased in comparison to the nanoporous permeation layer formulation (4012-1). Conversely, the ability of a relatively small (46-mer) oligonucleotide to be immobilized by a biotin-streptavidin interaction was sufficiently high in the nanoporous permeation layer, and actually decreased slightly in the mesoporous permeation layer. Although the invention is not bound by any particular theory, these results suggest that, perhaps, its increased rate of migration through the increased porosity layers, under electronic addressing conditions, decreased the opportunities for the biotinylated 46-mer to interact with the streptavidin attachment moieties. This hypothesis was strengthened by experiments incubating the four permeation layers with the 46-mer under passive conditions, under which no difference in immobilization was seen. Similar results were demonstrated with a wider range of range of porogen concentration formulations in the experiments described in Example 7, and shown in FIGS. 15 and 16.

Figure 13:
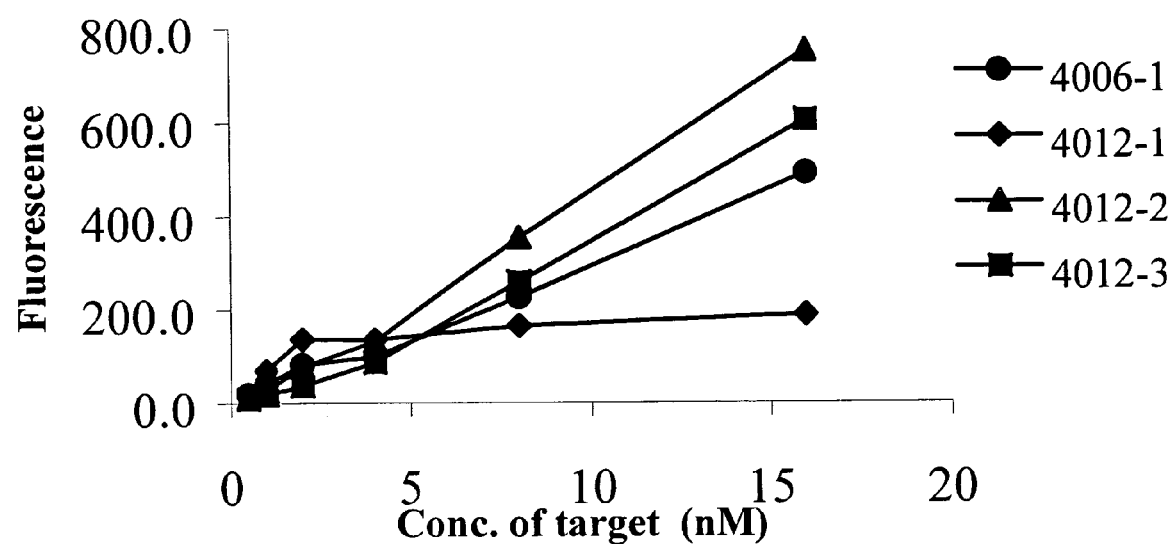
FIG. 13: A chart showing MFI readings from primer extension assay experiments described in Example 6, in which sample amplicons of 0.5 nM, 1.0 nM, 2.0 nM, 4.0 nM, 8.0 nM and 16.0 nM concentrations were addressed to multiple sites on chips with 4012-1, 4012-2, 4012-3, or 4006-1 permeation layer formulations. Note that the fluorescent intensity does not increase in a linear fashion with increasing nucleic acid concentration on the nanoporous permeation layer chip, 4012-1 (♦), but does increase in a linear fashion on the mesoporous permeation layer chips 4012-2 (▲), 4012-3 (■), and 4006-1 (●).

In a separate set of experiments, the four permeation layers were used in a primer-extension reporting assay format as described in Example 6. These experiments demonstrate the ability of the mesoporous synthetic hydrogel permeation layers to exhibit linearly increased hybridization and detection by enzymatic primer extension reporting using a moderately sized oligonucleotide (about 80 nt long, a typical size of those used in gene expression assays). As shown in FIG. 13, the fluorescent intensity on the mesoporous synthetic hydrogel permeation layers approximately doubled for every two fold increase oligonucleotide concentration over a wide concentration range, while it flattens out quickly on the nanoporous 4012-1 permeation layer. These results indicate that the mesoporous synthetic hydrogel permeation layer formulations provide improved performance for applications in which quantitative analysis is used, such as gene expression monitoring and viral load or pathogen concentration determinations.

The performance of 4006-1 formulation permeation layers on active electronic matrix chip devices was compared to a standard agarose-SA chip (MSP) in a SNP-type base-staking reporting assay (SNP1) as described in Example 4. As can be seen from the data in FIG. 11, the mean fluorescent intensity is very strong on the 4006-1 permeation layers, and is comparable to the MFI readings on the SA-agarose chip. In addition, all allelic probes show a strong signal, allowing clear discrimination between homozygous and heterozygous samples. The performance of this permeation layer formulation was further tested using seven other SNPs. As shown by the chart in Example 4, the mesoporous synthetic hydrogel permeation layer formulation 4006-1 provided excellent discrimination ratios between the signals for the allelic probes, and correctly identified all SNPs tested using amplified samples.

As these experiments were based on typical types of nucleic acid assays utilizing active electronic matrix chip devices, they have direct implications for use of the mesoporous synthetic hydrogel permeation layer devices of the present invention in similar nucleic acid hybridization-based assays and enzyme reaction or DNA-protein interaction based assays. As demonstrated by experimental data, mesoporous synthetic hydrogel permeation layers provide surprisingly improved detection performance and dynamic range, as compared to nanoporous standard synthetic polymer hydrogel formulations, making them suitable for a wide range of electronically assisted nucleic acid assay formats. As synthetic binding system applications such as pyranosyl-RNA encoding use similarly sized nucleic acid-like oligomers, although creating different secondary structures, the experimental results also indicate that the mesoporous synthetic hydrogel permeation layers will offer improved device performance in applications using synthetic binding systems. In addition, the performance of the new mesoporous synthetic hydrogel permeation layer devices in nucleic acid assays, especially the enzymatic reaction assays, indicate that they will also exhibit improved performance in protein-based applications such as immunoassays.

Porosity Control in Synthetic Polymer Hydrogel Permeation Layers

As described above, the improved characteristics of the mesoporous synthetic hydrogel permeation layer devices of the invention depend upon the presence of mesopores in the synthetic polymer hydrogel permeation layer on the devices. Thus, a key step in the production of the mesoporous synthetic hydrogel permeation layer is the control of porosity in the polymerizing hydrogel matrix, when the monomers and cross-linkers are polymerized into a polymer network. Practically, various porosities can be accomplished in two ways: a) producing a relatively physically homogeneous hydrogel matrix structure in which the spaces between the polymer matrix are of a sufficient distance to produce pores of the desired size, and b) producing a relatively physically heterogeneous synthetic polymer hydrogel matrix structure by encouraging the developing polymer strands to cluster into dense areas and void areas, usually by forming the matrix around a removable template structure of an appropriate size. Either strategy may be utilized alone, or in combination with the other, to produce the mesoporous synthetic hydrogel permeation layer devices of the invention.

Physically Homogeneous Methods: Polymerization Control

Synthetic polymer hydrogels are porous to a greater or lesser extent by nature, consisting primarily of a random network of cross-linked polymer strands, and an aqueous solution filling the spaces between the strands. This hydrated network creates a semi-solid structure, which has porosity characteristics primarily determined by the conditions of polymerization, including: total concentration of monomers (e.g., individual monomer moieties or block co-polymer units) and any cross-linker molecules in the polymerization mixture, the relative percentage of cross-linking agent (often a molecule with two or more polymerizable groups) in the polymerization mixture, and the rate of polymerization (which can be effected by the type, concentration, and activation of an initiator molecule, the temperature of the polymerization reaction, and other known parameters).

The type of synthetic polymer hydrogel utilized in the mesoporous synthetic polymer hydrogel permeation layers of the invention is not intended to be limited to acrylamide-chemistry hydrogels, although acrylamide/bisacrylamide systems are utilized as an exemplary synthetic polymer hydrogel system in the examples. In general, any sufficiently hydrophilic and polymerizable molecule may be utilized in the production of a synthetic polymer hydrogel for use as a permeation layer. Polymerizable moieties in the monomers may include alkenyl moieties including but not limited to substituted or unsubstituted $\alpha,\beta$,unsaturated carbonyls wherein the double bond is directly attached to a carbon which is double bonded to an oxygen and single bonded to another oxygen, nitrogen, sulfur, halogen, or carbon; vinyl, wherein the double bond is singly bonded to an oxygen, nitrogen, halogen, phosphorus or sulfur; allyl, wherein the double bond is singly bonded to a carbon which is bonded to an oxygen, nitrogen, halogen, phosphorus or sulfur; homoallyl, wherein the double bond is singly bonded to a carbon which is singly bonded to another carbon which is then singly bonded to an oxygen, nitrogen, halogen, phosphorus or sulfur; alkynyl moieties wherein a triple bond exists between two carbon atoms.

Acryloyl or acrylamido monomers such as acrylates, methacrylates, acrylamides, methacrylamides, etc., are advantageous because of the large body of knowledge which has been accumulated concerning the formulation of hydrogels using these polymers. More preferred acrylamido monomers include acrylamides, N-substituted acrylamides, N-substituted methacrylamides, and methacrylamide. However, other polymers are also useful, such as epoxide-based polymers, vinyl-based polymers, allyl-based polymers, homoallyl-based polymers, cyclic anhydride-based polymers, ester-based polymers, ether-based polymers, alkyleneglycol based polymers (e.g., polypropylene glycol), and the like. Thus, the mesoporous synthetic polymer hydrogel permeation layers of the invention encompass numerous synthetic polymer hydrogel compositions, which may be facilely devised by those of skill in the polymer arts. The primary considerations in selecting a synthetic polymer hydrogel are sufficient mechanical strength for use as a permeation layer, sufficient hydrophilicity to ensure sufficient solution volume in the gel, very low non-specific binding of biomolecules such as nucleic acids to the polymer hydrogel, and the adaptability of the synthetic polymer hydrogel to various methods for the production of mesoporous structures in the hydrogel matrix.

In preparing the polymerization mixture, it is possible to include within the permeation layer substances which can reduce the adverse physical and chemical effects of electrolysis reactions, including, but not limited to, redox reaction trapping substances (e.g., palladium for $H_2$, and iron complexes for $0_2$ and peroxides). A sub-layer of the permeation layer may be designed for this purpose. Additionally, the permeation layer can contain compounds or materials which help maintain the stability of the DNA hybrids; these can include but are not limited to histidine, histidine peptides, polyhistidine, lysine, lysine peptides, and other cationic compounds or substances.

For polyacrylamide based hydrogels, the relationship between the factors of monomer concentration, cross-linker percentage, polymerization conditions and porosity has been studied in the context of gel formulations for electrophoretic separations through the gel matrix, and one of skill in the art will appreciate the ability to manipulate the relative porosity of a polyacrylamide hydrogel using these parameters. In general, lowering the concentration of the total monomer concentration in the polymerization mixture will increase the porosity of the resulting hydrogel. However, lowering the concentration creates a less solid polyacrylamide hydrogel which lacks sufficient mechanical cohesion, and the maximum pore size obtainable through this method appears to be about 100 nm. Alternatively, the percentage of cross-linking agent can be increased to increase the porosity of the resulting gel. But, increasing cross-linker concentration produces a less hydrophilic polymer network, which eventually collapses and excludes the aqueous solution at higher cross-linker concentrations (e.g., about 30% for methylene bisacrylamide and about 50% for DHEBA). Even at these maximum workable concentrations, pore size may only be increased to about 200-300 nm. In addition, highly crosslinked polyacrylamide gels become increasingly friable, which also reduces the mechanical robustness of these synthetic polymer hydrogel formulations for use as a permeation layer. The use of different solvent systems has also been demonstrated to alter the porosity characteristics of synthetic polymer hydrogels. For example, the introduction of a less polar co-solvent, such as DMSO, may be used to form more porous networks of crosslinked polymer chains in polyacrylamide matrices.

In addition, applicants have discovered that the use of different copolymerizable attachment moieties (discussed in further detail below) can have a significant impact on the overall porosity of the resulting synthetic polymer hydrogel. For instance, in Example 3, switching from a SA-PEG-acryloyl molecule to an SA-N-acrylamide molecule increase the porosity of the 4006-1 formulation from a θ of about 3.0 to about 3.6. Thus, changes in the copolymerized attachment molecule in the polymerization mixture may also be utilized to increase the porosity of the resulting synthetic polymer hydrogel.

Thus, several techniques involving the basic formulation of the polymerization mixture have been exploited to increase polyacrylamide hydrogel porosity. However, even combinations of these techniques are only sufficient to generate pores in polyacrylamide hydrogels which are at the lower end of the mesopore size range. In addition, low-concentration polyacrylamide hydrogels with high cross-linker concentrations tend to be mechanically weak and friable, and can have undesirable hydrophobic characters. These materials may still be used as mesoporous synthetic hydrogel permeation layer compositions. But, for use as permeation layers, it is preferred that a physically heterogeneous polyacrylamide hydrogel be used, which may be formed by the methods described below.

It will, however, be appreciated by those of ordinary skill in the art that these mechanical limitations apply primarily to polyacrylamide hydrogels. The general principles of increasing porosity by decreasing monomer concentration and increasing cross-linker concentration may also be utilized to alter the porosity characteristics of other polymer hydrogels with fewer adverse mechanical strength effects. Thus, if a non-acrylamide polymer with a greater intrinsic mechanical strength is utilized, one may devise a physically homogeneous mesoporous synthetic hydrogel permeation layer composition which will have the desired mechanical strength.

Physically Heterogeneous Methods: Templating and Other Strategies

Because of the difficulties in obtaining a mechanically strong mesoporous synthetic hydrogel permeation layer formulation using physically homogeneous methods with acrylamide based synthetic polymer hydrogel, it is preferred that a physically heterogeneous structure strategy be utilized with this polymer material. In addition, because of the added control over pore size and distribution characteristics, these strategies are generally preferred to produce mesoporous synthetic hydrogel permeation layers for use in the present invention. Several tools for creating void spaces in synthetic polymer hydrogel matrices have been described in the context of electrophoretic separation materials and gel chromatography materials, including: the use of template porogens (e.g., micelles forming agents, solid mesobeads, liquid emulsions); the use of lateral aggregation of the polymer, and other methods such as bi-phasic copolymerizable systems.

In general, the use of templating porogens has allowed the greatest flexibility in producing synthetic polymer hydrogels with defined pore sizes. The basic process is simple: 1) a template of the desired size is mixed into the polymerization mixture; 2) the mixture is then polymerized, forming the network of polymerized cross-linked monomers around the template; 3) after polymerization, the template is selectively removed with a solvent solution, leaving behind the synthetic polymer hydrogel with the desired mesoporous structure. Thus, the primary consideration in choosing a templating porogen agent is the ability to selectively dissolve the agent in a solvent which will not significantly affect or alter the synthetic polymer hydrogel during the leaching process.

Several micelle-forming molecules are ideal for use as template porogens because they form spheroid structures with a fairly tight size distribution, and are usually extractable with relatively mild solvent conditions. The polymerization solution forms a two phase system with the micelle-forming templating agent: an "external" phase containing the polymerizable monomers and cross-linkers, and "internal" usually consisting primarily of the micelle forming materials. Compared to a simple immiscible emulsion system, in which the size of the non-polymerizing phase is less controlled or dependant on surfactant concentration, micelles are an ordered liquid structure with more definite size characteristics. Surfactants are particularly preferred as micelle-forming template porogens for use in producing mesoporous synthetic hydrogel permeation layers for use in the invention. By selecting the proper surfactant molecule, the desired micelle size range may be produced. For instance, nano-sized micelles are easily produced using sodium dodecyl sulfate (SDS), while meso-sized micelles may be produced using commercially available polymer-based nonionic surfactants such as the Brij series. Brij surfactants contain an aliphatic carbon chain and a polyether chain. These are versatile nonionic surfactants which can be used to create micelles of various sizes and size distributions. Brij 700 is utilized as an exemplary surfactant template porogen herein, but one of ordinary skill in the chemical arts would readily be able to utilize alternative micelle-forming template porogens in a similar manner.

Surfactant based template porogens have two other advantages, which are of great use in the manufacture of mesoporous synthetic hydrogel permeation layers on active electronic matrix devices. First, the size and number of pores produced, and thus the porosity characteristics of the synthetic polymer hydrogel, can be altered by changing the concentration of the surfactant template porogen in the polymerization mixture. As shown in FIG. 14, the porosity of a polyacrylamide synthetic polymer hydrogel may be altered by ~1.5 $\theta$ by modestly increasing amounts of surfactant. This ability to alter the $\theta$ value of the synthetic polymer hydrogel over a significant range is useful for the introduction of micropores into the mesoporous structure, which are preferred in mesoporous synthetic hydrogel permeation layers which will be used in large (over 100 nt) amplicon hybridization applications, or with enzyme reaction based applications.

Second, surfactant based template porogens are moderately soluble in water, allowing plain distilled water or aqueous buffer solutions to be utilized in leaching out the template after polymerization, as in the exemplar permeation layers. By avoiding the use of organic solvents or more chemically reactive compositions, the mechanical strength and mesostructural characteristics of the synthetic polymer hydrogel may be preserved. In contrast, non-water-soluble templating porogen agents usually require harsher leaching conditions, which can alter the structural integrity of the end-product permeation layer.

Instead of surfactants or other micelle forming templating porogens, a solid bead type templating porogen could be utilized. Sub-micron meso-size glass beads ("mesobeads") have been described which would make suitable porogen templates. These types of template porogens have the advantage of strict control over template size and size distribution, as this is a stable physical parameter of the solid beads, and the beads may be sorted by size prior to inclusion in the polymerization mixture. However, glass beads require leaching from the synthetic polymer hydrogel mesostructure by dissolution with hydrofluoric acid. In polyacrylamide gels, this process has not demonstrated an observable adverse effect on the gel structure. However, silicon dioxide layers are currently used in the substrate materials of active electronic matrix chip devices, and the exposure of these components to hydrofluoric acid could adversely affect the electrode array. Thus, the use of glass mesobeads is not a currently preferred method for the production of mesoporous synthetic polymer hydrogel permeation layer devices of the invention. However, if alternate non-etchable materials are utilized for the insulating layer (such as silicon nitride), or a non-silicon based substrate is used for the active electronic matrix electrode array, the disadvantages associated with the hydrofluoric acid leaching process would not be a concern.

Another alternate template porogen strategy is the use of immiscible liquids to form stable (or semi-stable) emulsions with the polymerization mixture. As many of the polymerization components (monomers, cross-linkers, copolymerizable attachment molecules) are soluble in an aqueous phase, it is popular to utilize a hydrophobic/hydrophilic two phase system, in which the hydrophobic phase forms droplets of the desired pore size in the hydrophilic phase. Usually, these emulsions are stabilized with surfactants to prevent aggregation and separation of the hydrophobic phase from the hydrophilic phase. Although this method is suitable for use in producing mesoporous synthetic polymer hydrogel permeation layers, it is not as preferred as the micelle-forming template porogen method, as the microemulsion droplets are not as ordered and well defined as the structure of surfactant micelles.

A similar strategy is the use of gas-phase porogen templates. Several porogens are known in the polymer arts which are useful in the production of gas bubbles during the polymerization reaction in a well distributed and controlled manner. The use of gas-producing porogen may be suitable for especially viscous polymerization mixtures in which the gas bubbles formed would not aggregate to a significant extent within the solidifying synthetic polymer hydrogel matrix. However, this method is not preferred for use with polyacrylamide hydrogels, as they are too fluid.

Non-templating strategies may also be utilized in order to introduce void spaces into the final synthetic polymer hydrogel matrix in order to create a physically heterogeneous mesostructure. For instance, a phenomenon called lateral aggregation has been described, wherein when polyethylene glycols of certain molecular weights are included in acrylamide polymerization mixtures, the growing polymer chains aggregate between the polyethylene glycol molecules. For instance, when PEGs in the range of 10,000 to 20,000 MW are added to the polymerization mixture at concentrations of about 2.0 to 2.5% wt/vol, pores of an average size of 500 nm may be produced (see, e.g., Righetti, et al., *J. Chromatography*, 638:165-178 (1993), incorporated fully herein by reference). Thus, the addition of high molecular weight PEGs may also be utilized to produce mesoporous synthetic polymer hydrogel permeation layers, especially those based on polyacrylamide hydrogels.

In addition, a controlled polymer network degradation technique has also been described. In this technique, a polyacrylamide matrix was degraded in a controlled manner by periodate oxidation in order to open micropores in the gel. However, this method would probably not be preferred for use on the devices of the invention, as the harsh chemical conditions may be detrimental to the electronics of the device or the attachment moiety chemistries.

As is evident from the above discussion, numerous methods exist to produce synthetic polymer hydrogel matrices with the desired mesoporous (and, optionally, microporous) character for use in the permeation layers of the invention. Thus, one of ordinary skill in the polymer arts will appreciate that the mesoporous synthetic polymer hydrogel permeation layers of the invention are not necessarily limited to layers produced by a particular method (e.g., the use template porogens), but rather encompass a broad class of mesostructured synthetic polymer hydrogel permeation layers which may be manufactured from a variety of synthetic polymer hydrogel materials by a variety of methods.

Synthetic Polymer Hydrogel Formulations with Copolymerization of Attachment Moieties Preferred synthetic polymer hydrogels for use in invention contain copolymerized attachment moieties for the attachment of specific binding entity molecules (e.g., nucleic acids, proteins, polypeptides, synthetic binding system components such as pyranosyl RNA). Such copolymerized attachment moieties can generally be described by general formula:

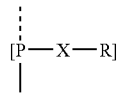

wherein,

P is at least one polymerizable moiety covalently attached to one or two moieties selected from the group consisting of: a monomeric unit of the synthetic polymer hydrogel and another P—X—R group, as defined herein, wherein the other P—X—R group may be the same as or different from the first P—X—R group, further wherein the dashed line is a covalent bond to the second moiety if P is covalently attached to two moieties;

X is a covalent bond or a linking moiety; and

R is a functional moiety for attaching, either covalently or non-covalently, a biomolecule.

The polymerizable attachment molecules, designated 'P—X—R', are incorporated into the permeation layer by copolymerization during fabrication of the permeation layer, or fabrication of a portion of the permeation layer, to produce a permeation layer containing copolymerized attachment moieties.

The X bond or linking moiety is typically a covalent bond or standard spacer or linker group. If X is not a covalent bond, X is preferably selected from the group consisting of an alkyl of 1-10 carbon atoms, an alkenyl of 2-10 carbon atoms, alkyl esters, ketones, amides, thioesters, alkyl ethers, amido groups, carbonyls, and/or any combinations thereof. In some preferred embodiments of the invention, X comprises a polyethylene glycol moiety, while in other preferred embodiments of the invention, X represents a covalent bond.

As used herein, alkyl denotes straight-chain and branched hydrocarbon moieties such as methyl, ethyl, propyl, isopropyl, tert-butyl, isobutyl, sec-butyl, neopentyl, tert-pentyl and the like. Such alkyls may be substituted with a variety of substituents including but not limited to hydroxy, oxo, amino, thio, cyano, nitro, sulfo and the like. Alkenyl denotes a hydrocarbon wherein one or more of the carbon-carbon bonds are double bonds and the non-double bonded carbons are alkyl or substituted alkyl. Alkenyl hydrocarbons groups may be straight-chain or contain one or more branches. Amino refers to moieties including a nitrogen atom bonded to 2 hydrogen atoms, alkyl moieties and combination thereof. Amido refers to moieties including a carbon atom double bonded to an oxygen atom and single bonded to an amino moiety.

The R moieties on the attachment molecule are preferably a moiety capable of participating in a biotin-binding pair reaction, i.e., either a biotin-moiety or a biotin-binding moiety. Biotin-binding moieties include anti-biotin antibodies; versions of avidin or streptavidin which have been genetically engineered, enzymatically cleaved, or chemically modified; and other synthetic biotin-binding structures which bind to biotin with a dissociation constant that is functionally equivalent to avidin or streptavidin. The R moieties in preferred embodiments of the present invention bind to derivatized biomolecules, which have been derivatized to contain either a biotin-moiety or a biotin-binding moiety (e.g., streptavidin). As many biomolecules may be readily derivatized with biotin or a biotin analog, in preferred embodiments of the invention R is a biotin-binding moiety such as, for example, streptavidin, avidin, or chemical or recombinantly engineered derivatives thereof. As will be appreciated by those of skill in the art, the attachment molecule may contain more than one P moiety attached to an R moiety, especially in the case of a proteinaceous R moieties such as streptavidin, which has a homotetrameric quaternary structure. In some preferred embodiments of the invention, the attachment molecule has about one P moiety for each biotin-binding site on R, while in other preferred embodiments, the attachment molecule has less than one P moiety for each biotin binding site on R.

The R moiety is utilized to attach biomolecules or other binding entities to the permeation layer at the microlocation. Several attachment chemistries (both non-covalent affinity chemistries and covalent reactive chemistries) have been developed for specifically derivatizing biomolecules such as nucleic acids, proteins, and polypeptides, an other molecules to allow for specific attachment to another moiety while retaining the activity of the derivatized molecule. Generally, these include, covalently bonded chemical moieties for non-covalent attachment such as streptavidin, biotin, phenyl boronic acid, salicylhydroxamic acid, or even synthetic binding entities such as specific pyranosyl RNA sequences (or "pRNAs," described in co-pending application Ser. No. 09/374,338 filed Aug. 13, 1999, herein incorporated fully by reference,) or reactive moieties for covalent attachment, such as N-hydroxysuccinimidyl active esters, amines, aldehydes, acyl chlorides, hydrazines, hydrazides, and the like. Derivatizations for attachment to R also include oligonucleotides containing oxidized ribose, amine terminations, or any of the well known bioconjugate pairs as outlined by Hermanson (Hermanson, G. T. *Bioconjugate Techniques* copyright 1996, Academic Press, San Diego, Calif.) herein incorporated by reference. Preferably, attachment of the chemical moieties for attachment to R to the biomolecule or other specific binding entity comprises a covalent bond. However, attachment of the derivatized biomolecules to a copolymerized attachment moiety in the permeation layer of the microarray may be through either a covalent or a noncovalent bond.

Thus, in alternative preferred embodiments, R is a reactive moiety for covalent attachment of a derivatized biomolecule by amine, hydrazine, or hydrazide attachment chemistries, such as an active N-hydroxyl succinimidyl (NHS) ester, a sulfonated NHS ester, an aldehyde, an acid, an acyl halide or the like, or a hydrazide, hydrazine, amine. Hydrazide attachment chemistries are detailed in PCT/US01/41663 (designating the US), which are useful to attach binding entities to the mesoporous synthetic hydrogel permeation layers of the devices of the invention. In addition, other reactive groups for use in common biomolecule attachment chemistries may be used, such as those suitable for disulfide linkages or thioester linkages (e.g., thiols), phosphorothiolate monoesters, acetals, ketones, aldehydes, dialdehydes, bromo- or iodo-acetamides, and esters. In addition, psoralens may be useful as R in various embodiments of the invention. Preferred psoralens for use are photoactivatable at a wavelength of about 365 nm.

In other alternative embodiments of the invention, R may be a synthetic pairing system unit, such as a pyranosyl-RNA oligomer, for immobilizing the specific binding entity at particular microlocations on the active electronic matrix device. In these embodiments, the pRNA may be derivatized with a polymerizable moiety and copolymerized into the mesoporous synthetic polymer hydrogel permeation layer as is generally described for P—X—R molecules. However, as described for copolymerized specific binding entities below, the use of a mold which produce permeation layers which cover just one microlocation electrode or a subset of microlocation electrodes, rather than an entire array of microlocation electrodes, is preferred.

As described for biotin binding moieties, such as streptavidin, R is usually copolymerized in an active state. However, especially when using reactive groups as R, R may be modified to require deprotection or activation in order to function as an attachment moiety. For instance, t-butyl or another bulky moiety may be used to shield a reactive R group during polymerization, and then cleaved prior to the attachment of the specific binding entities to the microlocations of the active electronic matrix device. Alternatively, R can be provided as a reactive group precursor in the co-polymerized molecule, and then converted (e.g., by an oxidation or reduction reaction) to the reactive group.

The P moiety may react with monomers of the surrounding permeation layer, or with P moieties of a second attachment molecule, and so forth. Thus, the attachment molecules to be added may also already be partially polymerized prior their incorporation into the base permeation layer (e.g., in the form of a block copolymer, or other additive unit). The polymerization reaction may be carried out in a solution, slurry, or other acceptable format, where the P moiety may react with a monomer moiety of the growing permeation layer polymer (which may be the same as 'P') and/or a P moiety of another attachment molecule. The polymerization of P into the permeation layer may be initiated nonspecifically by using a polymerization initiator molecule, such as a free radical polymerization initiator, that is sensitive to heat and/or specific wavelengths of electromagnetic radiation. The use of such activatable initiators allows the initiation of polymerization by an outside energy source (heat or a wavelength of light), which can be applied across the entire microelectrode array, or at specific portions of the microelectrode array.

P comprises a chemical moiety which includes a reactive center that may participate in bonding to another P reactive center in a polymerization reaction, and/or bond to a reactive center of the permeation layer polymer matrix. Additionally, P may bond to an R moiety of another functional group. P is preferably selected from the group consisting of alkenyl moieties including but not limited to substituted or unsubstituted α,β,unsaturated carbonyls wherein the double bond is directly attached to a carbon which is double bonded to an oxygen and single bonded to another oxygen, nitrogen, sulfur, halogen, or carbon; vinyl, wherein the double bond is singly bonded to an oxygen, nitrogen, halogen, phosphorus or sulfur; allyl, wherein the double bond is singly bonded to a carbon which is bonded to an oxygen, nitrogen, halogen, phosphorus or sulfur; homoallyl, wherein the double bond is singly bonded to a carbon which is singly bonded to another carbon which is then singly bonded to an oxygen, nitrogen, halogen, phosphorus or sulfur; alkynyl moieties wherein a triple bond exists between two carbon atoms. More preferred P include substituted or unsubstituted α,β,unsaturated carbonyls, vinyl, allyl and homoallyl groups and alkynes. P may also be selected from the group consisting of acetal, epoxide, ester, carboxylic acid, amide, halo-acetamide, thiol, phosphorothiolate monoester, thioester, disulfide, aldehyde, ketone, hydrazide, hydrazine, and amines. In more preferred embodiments, P is an acryloyl or acrylamido moiety. In especially preferred embodiments, P is an acrylamido moiety, and most preferably a methacrylamide moiety.

As will be appreciated by those of skill in the polymer arts, an appropriate P should be selected which will easily copolymerize with monomers of the synthetic polymer hydrogel matrix, in order to ensure even distribution and good incorporation of the attachment moieties throughout the synthetic polymer hydrogel permeation layer. Generally, the use of a P which is the same as or similar to the monomer of the polymerization mixture will produce a better copolymerized attachment moiety containing mesoporous synthetic polymer hydrogel permeation layer. Thus, in the examples below, an acryloyl or acrylamido moiety is used as P, for copolymerization into an acrylamide hydrogel.

Copolymerized Specific Binding Entities

In alternative preferred embodiments of the invention, the mesoporous synthetic polymer hydrogel permeation layer comprises copolymerized specific binding entities. In these embodiments, the copolymerized specific binding entity has the same general formula:

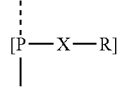

as defined above, with the change that R is a specific binding entity. As discussed, specific binding entities useful for assays performed on the active electronic matrix chip devices of the invention include, but are not limited to, nucleic acids, proteins, polypeptides, proteoglycans, glycoproteins, antigenic epitopes, and other molecules useful in biochemical or chemical assays. Preferred specific binding entities include nucleic acids (e.g., DNA, RNA, chemically derivatized DNA or RNA, or nucleic acid analogs which hybridize with naturally occurring nucleic acids), proteins, antibodies, and antigens. As demonstrated by the copolymerization of streptavidin in the polyacrylamide mesoporous synthetic polymer hydrogel permeation layers of the examples, proteins and polypeptides may be readily derivatized with acryloyl or acrylamido groups (or other polymerizable moieties), and copolymerized with minimal loss of protein activity. In addition, several phosphoramidite reagents are available to facilely attach a copolymerizable moiety, such as an acryloyl or acrylamido group, to either end of nucleic acids (e.g., Acrydite™ from Mosaic Technologies, Boston, Mass.). Thus, specific binding entities may be incorporated into the permeation layer directly by copolymerization.

Because one usually does not wish to have the same specific binding entity at each microlocation of an active electronic matrix device, it is advantageous to use molds for polymerizing the permeation layer onto the active electronic matrix microelectrode array which are sized to produce a permeation layer over one microlocation or a sub-set of microlocations on the active electronic matrix device. Such molds may easily be designed for an array of electrodes as pictured in FIG. 1, wherein a plurality of mold cavities are provided in the mold which align with specific microelectrodes on the device. For instance, such molds may comprise an array of mold cavities of an appropriate shape which at least cover the individual microlocation electrodes of the active electronic matrix chip device (for instance, 100 round, square, or hexagonal cavities which are at least 80 µm in diameter for the electrodes in FIG. 1). Or, molds may be produced which comprise cavities which cover a sub-set of microlocation electrodes (e.g., an entire row, or a square of 4 electrodes, etc.). The polymerization mixture comprising a particular copolymerizable specific binding entity may then be pipetted into those mold cavities which correspond to the microelectrodes of the array which are to be covered with a mesoporous synthetic polymer hydrogel permeation layer comprising the particular specific binding entity. Such molds may be fabricated in quartz, glass, or other materials using standard microlithographic techniques, or may be molding in plastics from a master created using such techniques.

The use of copolymerized specific binding entities is particularly attractive for the production of clinical application active electronic matrix chip devices, in which several pre-loaded specific binding entities may be provided to test for a panel of particular nucleic acid sequences, antibodies, or antigens in a sample. As clinical users have an interest in convenience and time-savings for test devices, such pre-loaded active electronic matrix chip devices offer significant advantages over generic devices which must be loaded with specific binding entities by the consumer. In addition, the copolymerized specific binding entity devices of the invention are also useful in research contexts in which several samples will be assayed for the same nucleic acid sequences, antibodies, or antigens in a several samples for comparison. By copolymerizing the specific binding entity into the permeation layer over a set of microelectrodes, the specific binding entity concentration is standardized for that set of microlocations, allowing for more rigorous comparison of the binding of the analyte between samples. Because the micromolding process lends itself readily to automated steps in which polymerization mixtures containing the particular copolymerizable specific binding entities (e.g., particular nucleic acid probes covalently linked to an acryloyl moiety) can be interchanged, the manufacture of custom pre-loaded chips for particular research experiments may be easily realized.

Basic Active Electronic Matrix Chip Design

In order for an active electronic matrix chip device to carry out multi-step and multiplex reactions, its electronic components must be able to maintain active operation in aqueous solutions. To satisfy this requirement, each microlocation has an underlying controllable and functioning DC micro-electrode. However, it is important for device performance, particularly sensitivity (signal to noise ratio), that binding and affinity reactions are not prevented by the electrolysis reactions occurring on the active DC electrode surfaces. In addition to the damaging effects incurred by any of the sensitive reagents and analytes (DNA, RNA, proteins, etc.) directly contacting the electrode surface, the electrodes produce electrolysis products which include acid ($H^+$), base ($OH^-$), hydrogen, oxygen, and various free radical species which can also damage the sensitive components. Other considerations for the design and fabrication of a device include, but are not limited to, materials compatibilities (including compatibility with the permeation layer and its manufacture, and solution components utilized in various chemical or biochemical assays on the device), nature of the specific binding entities and the subsequent reactants and analytes, and the number of microlocations.

By "a controllable and functioning DC mode microelectrode" is meant a micro-electrode biased either positively or negatively, operating in a direct current mode (either continuous or pulse or DC/AC), which can in a controllable manner affect or cause the free field electrophoretic transport of charged specific binding entities, reactants, or analytes to or from any location on the device, or from the sample solution.

As described herein, the free field electrophoretic "transport" of molecules is not dependent on bounding or confining the electric field produced by an insulating material. Conventional electrophoretic separation technologies require confinement or enclosure of electric field lines by insulating (non-conducting) materials (e.g., the sides of a glass capillary tube in capillary gel electrophoresis). In the case of free field electrophoretic transport on active electronic matrix chip devices, charged molecules are moved from one microlocation through the bulk solution volume to any other microlocation, or from the bulk solution to specific microlocations. Therefore, special arrangements or confinement by insulating materials is not required for this aspect of the invention. However, the relatively small area of the microlocation test site allows high current densities to be produced. These high current densities over a confined area of the chip allow for the rapid concentration of the charged nucleic acids or other biomolecules from solution and electronic stringency for de-hybridization.

An active electronic matrix chip device can be designed to have as few as two addressable microlocations or as many as hundreds of thousands of microlocations. In general, a complex device with a large number of microlocations is fabricated using microlithography techniques or combination of microfabrication and micromachining. Fabrication is carried out on silicon or other suitable substrate materials, such as glass, silicon dioxide, plastic, insulated metallic or ceramic materials. These microelectronic "chip" designs would be considered large scale array or multiplex analysis devices.

FIG. 1 shows the electrode array of a 100 site NanoChip® device, produced using photolithographic techniques. The microlocations are the areas in and on the permeation layer above the exposed metal electrode pads, which have been deposited on an insulator layer/base material. The metal pads serve as the underlying micro-electrode structures. Electrode materials can include but are not limited to: aluminum, copper, carbon, iron, silver, gold, palladium, platinum, titanium, tungsten, polysilicon, and indium tin oxide, as well as silicide materials such as platinum silicide, titanium silicide, gold silicide, or tungsten silicide. Special techniques known in the art for ensuring proper adhesion to the insulating substrate materials ($SiO_2$) are used with different metals. Various metals and other materials may be used for different conductive components of the device, for example, using aluminum for the perimeter contact pads, titanium for the interconnect circuitry, and a noble metal (gold or platinum) for the micro-electrodes. In addition, it may be advantageous to use a layered electrode structure, in which a surface layer of a less reactive noble metal, or noble metal alloy is layered over another metal layer. For instance, in the electrodes shown in FIG. 1, the electrode is platinum deposited onto a support layer of titanium/tungsten alloy (for improved adhesion). Alternatively, conductive polymers such as polyanilines or polypyrrolidines may be used as electrode materials. In addition to the electrodes underlying the microlocations of the active electronic matrix chip devices, other electrodes may be provided which do not underlie microlocations on the chip devices. These include, for example, counter electrodes which are simply used as a counter-biased electrode during the electrophoretic transport of the biomolecules in the solution. As they are not utilized as microlocation electrodes, they are usually not covered by the permeation layer. An example of these electrodes is shown in FIG. 2, in which the counter electrodes are positioned in a circle surrounding the center array of microelectrode pads underlying the microlocations of the chip device. In addition to the counter electrodes, other electrodes, such as reference or pseudo-reference electrodes (e.g., silver paste electrodes, etc.) for use in measuring and maintaining constant current or voltage supplied to the electrodes, may be incorporated into the chip device.

On the surface of the finished chip device, an insulator material separates the metal electrode pads from each other in the plane of the chip device. This separation of the electrodes by the insulating material prevents the "short circuiting" of the electron current through the surface of the chip device, rather than being directed through the solution over the chip device. Generally, the insulator material (e.g., silicon dioxide) is a layer deposited over and between the metal layer deposited on the substrate, or a sandwich-type electrode and lead wire structure, as shown in FIG. 1. In this manufacturing strategy, the insulating layer deposited above the electrode pads is removed to expose the functioning micro-electrodes. This can be more easily seen in FIG. 2, where the exposed electrode sections appear as darker circles above the conductive electrode material. The darkened appearance is caused by increased depth of the permeation layer in the etched "holes" in the insulating silicon dioxide layer. However, other manufacturing strategies will be apparent to those in the microelectronic arts. Insulator materials include, but are not limited to, silicon dioxide, silicon nitride, glass, resist, polyimide, rubber, plastic, or ceramic materials. The microelectrodes on the NanoChip® device shown are separated by a silicon dioxide layer, which also covers and insulates the micro wiring which connects the electrode pads to electrical connections on the perimeter of the chip (outside of FIG. 1).

Thus, the basic features of an individual microlocation formed by microlithographic techniques are: the metal pad, which defines the location of the addressable microlocation, and which may incorporate a layer for the covalent attachment of the permeation layer; a permeation layer overlaying the microelectrode; an attachment layer, which may be coextensive with the permeation layer, or another layer of attachment-moiety laden permeation layer material overlaying a base permeation layer.

The thickness of the permeation layer for microlithographically produced devices can range from approximately 1 nanometers (nm) to 100 microns ($\mu$m), with 2 nm to 10 $\mu$m being the most preferred. Generally, in preferred embodiments of the permeation layers of the invention, the permeation layers are between about 0.5 $\mu$m and about 10 $\mu$m thick in the dry state, more preferably between about 1.0 $\mu$m and about 5.0 $\mu$m thick in the dry state, and most preferably between about 1.0 $\mu$m and about 2.0 $\mu$m thick in the dry state (or at least about 8-9 $\mu$m thick when in equilibrium with aqueous buffer). Also, in preferred embodiments, the permeation layers vary in thickness across the electrode array of the active electronic matrix chip device by less than 0.5 $\mu$m, more preferably by less than 0.2 $\mu$m, and most preferably by less than 0.1 $\mu$m, as measured in the dry state.

As mentioned above, synthetic polymer hydrogel permeation layers may be molded onto the active electronic matrix microelectrode array as a single layer, or as a plurality of layers. In some cases, the permeation and attachment layers can be formed from the same material, as demonstrated in the Examples. Alternatively, a base permeation layer may be molded onto the microelectrode array, followed by a permeation layer containing copolymerized attachment moieties or copolymerized specific binding entities. When more than one layer forms the permeation layer, it is preferred that subsequent layers be covalently attached to (or grafted onto) the previous layer. The use of multi-layer permeation layers is especially preferred when using higher cost or specialty reagents, such as copolymerizable specific binding entities.

Optimally, the attachment layer has from $10^5$ to $10^7$ attachment moieties (or specific binding entities, after attachment) per square micron ($\mu m^2$) for the attachment of specific binding entities. Thus, when copolymerized attachment moieties are provided in the mesoporous synthetic polymer hydrogel permeation layer devices of the invention, they should be present at sufficient concentration in the polymerization mixture to provide a density of attachment sites within this range. The attachment of specific binding entities should not overcoat or insulate the surface so as to prevent the underlying micro-electrode from functioning. A functional device requires some fraction (~5% to 25%) of the actual metal micro-electrode surface to remain accessible to solvent ($H_2O$) molecules through the permeation layer, and to allow the diffusion of counter-ions (e.g., $Na^+$ and $Cl^-$) and electrolysis gases (e.g., $O_2$ and $H_2$) to occur. The intermediate permeation layer is also designed to allow diffusion to occur. Additionally, the permeation layer should have a pore limit property which inhibits or impedes the larger binding entities, reactants, and analytes from physical contact with the micro-electrode surface. Thus, the permeation layer keeps the active micro-electrode surface physically distinct from the binding entity layer of the microlocation.

Addressable microlocations can be of any shape (e.g., such as round, square, or rectangular.) The size of an addressable microlocation can be of any size, preferably range from sub-micron (∥0.5 $\mu$m) to several centimeters (cm), with 5 $\mu$m to 100 $\mu$m being the most preferred size range for devices fabricated using microlithographic techniques. The microlocation size for the device shown in FIG. 1 is 80 $\mu$m. The spacing between microlocations is determined by the ease of fabrication, the requirement for detector resolution between microlocations, and the number of microlocations desired on a device. For instance, the distance between the microlocations of the chip device shown in FIG. 2 is 120 $\mu$m edge to edge, or 200 $\mu$m center to center. However, particular spacings between microlocations, or spatial arrangement or geometry of the microlocations, are not necessary for device function, in that any combination of microlocations (i.e., underlying micro-electrodes) can operate over the complete device area. As the number of microlocations increases beyond several hundred, the complexity of the underlying circuitry of the microlocations increases. In this case the microlocation grouping patterns have to be changed and spacing distances increased proportionally, or multi-layer circuitry can be fabricated into the basic device, i.e., transistors and semiconductor control elements incorporated directly into the silicon. As mentioned above, connective circuitry for each individual underlying micro-electrode preferably runs to an outside perimeter of metal contact pads. When these contact pads are produced in a standard configuration, the chip device can be mounted in a standard quad package, and the chip contact pads wired to the quad package pins.

It is not necessary to enclose the device or completely confine the microlocations with dielectric or insulating barriers because complex electronic field patterns or dielectric boundaries are not required to selectively move, separate, hold, or orient specific molecules, in the space or medium between any of the electrodes. The active electronic matrix accomplishes spatial separation by attaching the specific binding molecules and subsequent analytes and reactants to the surface of an addressable microlocation. However, it is preferred that the active electronic matrix chip devices of the invention be contained, or packaged, within a flow-cell to allow for the controlled introduction of samples and reagents onto the surface of the devices. In general, it is preferred that such flow cells comprise a closed volume over the active electronic matrix chip device with at least one input port and at least one output port. In this manner, the functions of sample introduction, rinsing, and- reagent introduction may be easily carried out on the active electronic matrix chip devices using standard fluidics techniques.

Systems containing more than one chip and additional packaging and peripheral components may be designed to address problems related to clinical diagnostics (i.e., addition of sample materials, fluid transfer, and containment of bio-hazardous materials, and the detection of labeling moieties such as, for example, fluorescent, chemiluminescent, colorigenic, or radioactive moieties.) The packaged chip can then be plugged into a microprocessor controlled DC power supply and multimeter apparatus which can control and operate the device. It is contemplated by this invention that device manufacture (prior to addressing) may involve the incorporation of various basic components into a disposable device which would be essentially sandwiched together in an assembly such as: the basic chip device to which the binding entities are attached; a flow cell fluid containment component; and, optionally, on board active electronic matrix controller component. This strategy solves a number of problems related to fabrication techniques and materials compatibilities.

Anchoring Chemistries for the Permeation Layer

Although synthetic polymer hydrogel materials such as those noted above have desired functional qualities, hydrogel permeation layers are prone to separate or 'delaminate' from the electrode surface. Although the applicants are not bound by any particular theory, this delamination is thought to be caused by a change in the chemical make-up at the interface between the permeation layer and the electrode resulting from the application of electronic potential at the electrode and by physical disruption from charged ions and gases emanating from the electrode. Such delamination can be viewed from the standpoint of 'microdelamination' and 'macrodelamination'.

Microdelamination involves the electrochemical degradation of the chemical interface between the permeation layer and the electrode itself. It is observed by the formation of raised bulges in the permeation layer, or by ringlets visible due to defraction of light from the delaminated layer when appropriately viewed by a confocal microscope and results in the loss of consistency in permeation layer performance (possibly due to the loss of control over the electric field uniformity). Macrodelamination, on the other hand, is caused by a mismatch of the surface energies between the permeation layer and the chip substrate and results in permeation layer peeling (lift-off) which can extend across the entire microchip surface. Since the permeation layer provides a means for the attachment of specific binding entities for analytes present in the liquid overlay, macrodelamination is detrimental to assays typically run on the active electronic matrix chip devices. In preferred embodiments of the synthetic polymer hydrogel active electronic matrix chip devices of the invention, the problem of micro- and macrodelamination may be alleviated by the use of a covalent chemistry linkage between the active electronic matrix electrode array and the permeation layer hydrogel matrix. This chemistry is applicable to a variety of permeation layer synthetic polymer hydrogel compositions, including polyacrylamides, and is able to withstand current densities of at least 0.04 nA/$\mu$m$^2$ and/or voltage drops between 1 and 3 V.

In the case of metals like aluminum or silicon/noble metal mixtures, the metal oxide layer provides a base for the covalent coupling of the permeation layer. Metal oxide and hydroxyl groups (either alone or in combination), and other similar interface surfaces known to those skilled in the art of surface coating chemistries provide covalent sites from which to construct or hold the permeation layer. Preferred metal/silicide electrodes include platinum silicide (PtSi), tungsten silicide (WSi), titanium silicide (TiSi), and gold silicide (AuSi), as they provide sites which may be readily utilized for silane coupling using the reagents noted below.

However, it is not essential that the permeation layer be covalently anchored to the metal electrode surface. Significant additional resistance to micro- and macro-delamination may be obtained by simply attaching the permeation layer to the substrate or insulating material surrounding the actual microelectrode of the microlocation. The physical overlaying of permeable materials represents an alternative method which is also within the scope of this invention. Thus, in some preferred embodiments, the synthetic polymer hydrogel permeation layers of the devices of the invention are covalently anchored to the substrate of the active electronic matrix device which surrounds the microelectrode. As used to describe this method, the "substrate" is considered to include not only a layer of support material that the microelectrode is formed on, but also any insulating material layers (e.g., silicon dioxide) which may overly the metal of the electrode and thus define the boundary of the microlocation. For example, in the case of metals like platinum and gold, a permeation layer can be physically overlaid, and then anchored to the silicon dioxide layer surrounding the electrode. This "tenting" approach, described in Example 1, has proven very useful in preventing macrodelamination of the permeation layer. The use of cross-linking agents to anchor a permeation layer to an electrode of an active electronic matrix chip device is generally described in U.S. Pat. No. 6,303,082, incorporated fully herein by reference.

In an example of these preferred embodiments, the covalent attachment comprises a linking moiety that provides an moiety for bonding the linker to the silanol moiety of a silicon bearing surface (e.g., a metal/Si electrode or a silicon containing surface of the substrate) and a separate moiety for bonding the linker to the permeation layer. In a particularly preferred embodiment, the linking moiety is defined by the formula:

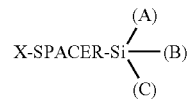

where X=acrylate, methacrylate, acrylamide, methacrylamide, allyl, vinyl, acetyl, amine (substituted or not), epoxy or thiol;

SPACER=alkyl, aryl, mono- or polyalkoxy (such as ethyleneglycol or polyethyleneglycol), mono- or polyalkylamine, mono- or polyamide, thioether derivatives, or mono- or polydisulfides;

A and B=any combination of Oxygen-R, where R=H, alkyl such as methyl, ethyl, propyl, isopropyl or other linear or branched hydrocarbon, Cl, Br or a moiety functionality similar to that of X-SPACER; and C=Oxygen-R, where R=H, alkyl such as methyl, ethyl, propyl, isopropyl or other linear or branched hydrocarbon, Cl, Br, or any other hydrolyzable moiety.

In embodiments where metal/Si microlocation electrodes are used, the silanol moiety can react with hydroxyl groups bonded to a silicon moiety of the electrode surface. In embodiments where a silicon-containing group is not present on the electrode, but is present on the substrate, the silanol moiety can react with hydroxyl groups bonded to a silicon moiety on the substrate surface. On the other end of the linker, the X moiety comprises chemical groups that are available to covalently react with reactive centers of the permeation layer polymer.

Figure 4:
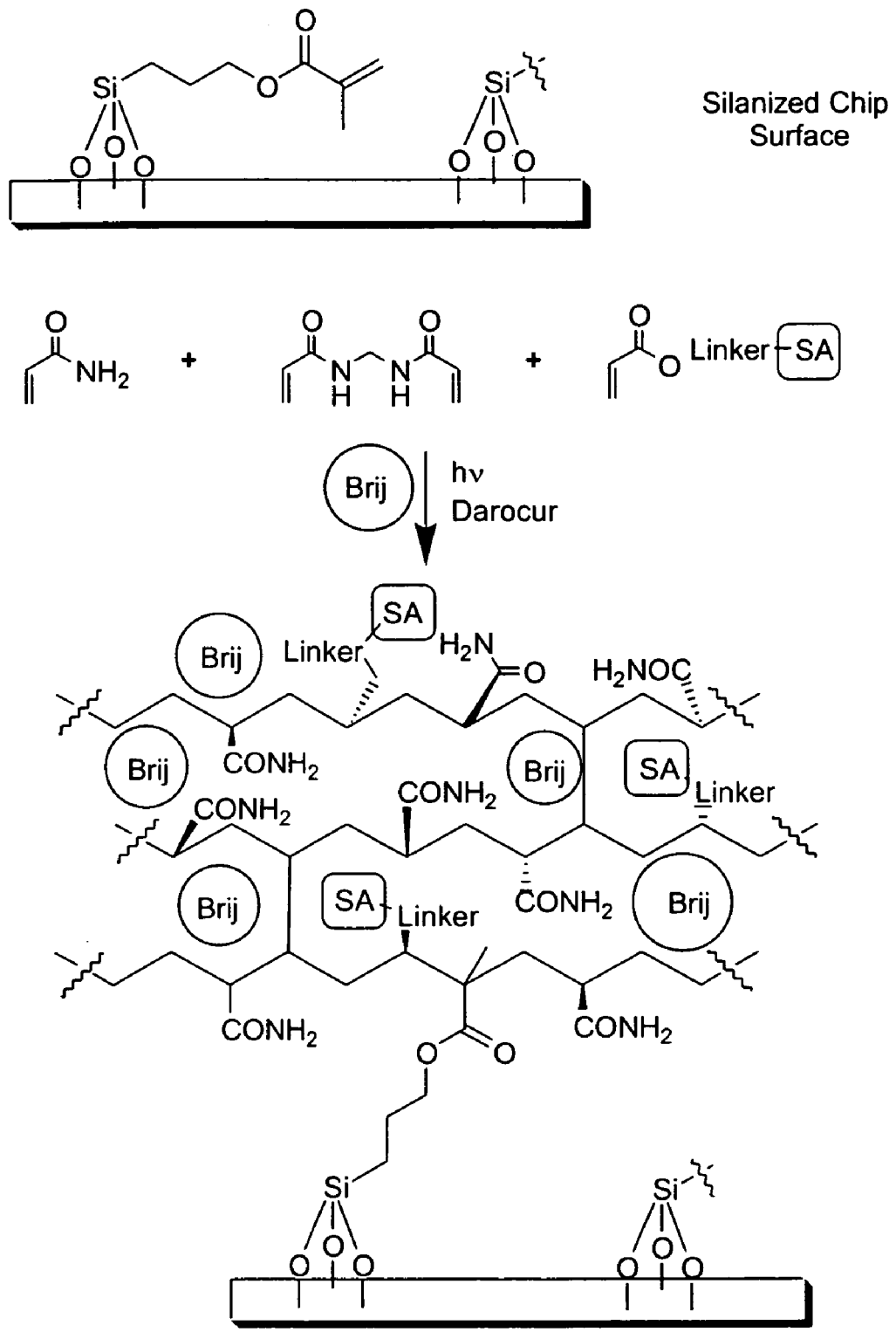
FIG. 4: A reaction scheme illustrating the copolymerization of an acryloyl-PEG-SA derivative with acrylamide in the presence of Brij micelles to form a mesoporous acrylamide crosslinked hydrogel impregnated with SA attachment moieties. Note that when the polymerization takes place above an active electronic array device with a surface which has been activated with a linker silane derivative (such as Bind Silane™, also 3-methacryloxy-propyl-trimethoxysilane), the polymer hydrogel matrix becomes covalently linked to the surface of the device by incorporation of the linker moiety into the polymer.

As shown in FIG. 4, the permeation layer may be linked to the electrode by a linking moiety that has at least one copolymerizable reactive center. Linkers having suitable characteristics are provided in the Table below:

be first treated with an argon plasma for 5 minutes at 250 mTorr and 250 Watts. The chip may then be treated with the linker by vapor deposition over 15 minutes at room temperature then cured onto the chip by heating for 2 hours at 90° C. This causes the linker to covalently bind to the hydroxyl groups of the silicide moiety in the electrode. Once the linker is attached to the microchip, a UV-initiated free radical polymerization reaction can be conducted between the monomers which will make up the permeation layer and the vinyl moieties present at the surface of linker-derivatized electrodes, thereby synthesizing the permeation layer and covalently anchoring it to the electrode in a single step.

Applications Utilizing Active Electronic Matrix Devices With Mesoporous Synthetic Hydrogel Permeation Layers In general, the mesoporous synthetic hydrogel permeation layer devices of the present invention may be addressed and used in much the same manner as previously disclosed active electronic matrix chip devices. A description of the

| CHEMICAL TYPE | FORMULA |
|---|---|
| ACRYLATES: | $CH_2=CHCOOCH_2CH_2CH_2Si(OCH_3)_3$ |
| | $CH_2=CHCOOCH_2CH_2CH_2SiCl_3$ |
| | $CH_2=CHCOOCH_2CH_2CH_2Si(CH_3)(OCH_3)_2$ |
| | $CH_2=CHCOOCH_2CH_2CH_2Si(CH_3)_2(OCH_3)$ |
| | $CH_2=CHCOOCH_2CH_2CH_2Si(CH_3)Cl_2$ |
| | $CH_2=CHCOOCH_2CH(OH)CH_2NHCH_2CH_2CH_2Si(OC_2H_5)_3$ |
| METHACRYLATES: | $CH_2=C(CH_3)COOCH_2CH_2CH_2Si(OCH_3)_3$ (MOTS) |
| | $CH_2=C(CH_3)COOCH_2CH_2CH_2SiCl_3$ |
| | $CH_2=C(CH_3)COOCH_2CH_2CH_2Si(CH_3)(OCH_3)_2$ |
| | $CH_2=C(CH_3)COOCH_2CH_2CH_2Si(CH_3)_2(OCH_3)$ |
| | $CH_2=C(CH_3)COOCH_2CH_2CH_2Si(CH_3)Cl_2$ |
| | $CH_2=C(CH_3)COOCH_2CH(OH)CH_2NHCH_2CH_2CH_2Si(OC_2H_5)_3$ |
| ACRYLAMIDES: | $CH_2=CHCONHCH_2CH_2CH_2Si(OC_2H_5)_3$ (AMPTS) |
| | $CH_2=CHCONHCH_2CH_2CH_2SiCl_3$ |
| | $CH_2=CHCONHCH_2CH_2CH_2Si(CH_3)(OCH_3)_2$ |
| | $CH_2=CHCONHCH_2CH_2CH_2Si(CH_3)_2(OCH_3)$ |
| | $CH_2=CHCONHCH_2CH_2CH_2Si(CH_3)Cl_2$ |
| | $CH_2=CHCONHCH_2CH(OH)CH_2NHCH_2CH_2CH_2Si(OC_2H_5)_3$ |
| | $CH_2=CHCONHCH_2CH_2CONHCH_2CH_2CONHCH_2CH_2CH_2Si(OC_2H_5)_3$ |
| METHACRYLAMIDES: | $CH_2=C(CH_3)CONHCH_2CH_2CH_2Si(OCH_3)_3$ |
| | $CH_2=C(CH_3)CONHCH_2CH_2CH_2SiCl_3$ |
| | $CH_2=C(CH_3)CONHCH_2CH_2CH_2Si(CH_3)(OCH_3)_2$ |
| | $CH_2=C(CH_3)CONHCH_2CH_2CH_2Si(CH_3)_2(OCH_3)$ |
| | $CH_2=C(CH_3)CONHCH_2CH_2CH_2Si(CH_3)Cl_2$ |
| | $CH_2=C(CH_3)CONHCH_2CH(OH)CH_2NHCH_2CH_2CH_2Si(OC_2H_5)_3$ |
| ALLYL DERIVATIVES: | $CH_2=CHCH_2NHCH_2CH_2CH_2Si(OCH_3)_3$ |
| | $CH_2=CHCH_2SiH(OCH_3)_2$ |
| | $CH_2=CHCH_2Si(CH_3)_2Cl$ |
| | $CH_2=CHCH_2SiHCl_2$ |
| | $CH_2=CHCH_2Si(OCH_3)_3$ |
| AMINO DERIVATIVES: | $H_2NCH_2CH_2NHCH_2CH_2CH_2Si(OCH_3)_3$ (AEAPS) |
| | $H_2NCH_2CH_2CH_2CH_2CH_2CH_2NHCH_2CH_2CH_2Si(OCH_3)_3$ (AHAPS) |
| | $H_2NCH_2CH_2CH_2Si(OCH_3)_3$ (APS) |
| | $H_2NCH_2CH_2CH_2Si(OC_2H_5)_3$ |
| EPOXY DERIVATIVES: | 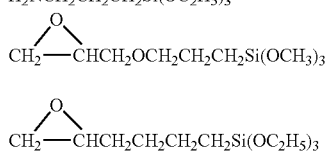 |

In a particularly preferred embodiment, active electronic matrix chips having covalent attachment chemistry use a linker selected from the group consisting of: APS, AEAPS, AHAPS, MOTS, and AMPTS.

Example 1 illustrates the use of a silanol linker to anchor the permeation layer to the substrate surrounding a platinum microlocation electrode. Alternatively, if a noble metal/silicide electrode is used, the electrode array of the chip may electronic addressing procedure may be found in U.S. Pat. No. 6,051,380. Briefly, the devices may be addressed by introducing a solution containing an attachment-derivatized molecular species to be addressed onto the active electronic matrix chip device (usually in a flow-cell compartment), and biasing the electrodes under the microlocations to which the molecular species is to be addressed, so that the electrode is biased opposite the charge of the molecular species (e.g., positive if the molecular species is a nucleic acid). The molecular species then migrates through the solution to the microlocation, and becomes attached via the attachment-facilitating moiety to an attachment moiety in the permeation layer (e.g., through a biotin-streptavidin interaction). As described in U.S. Pat. No. 5,051,380, preferred solutions for use are low-conductance buffers with significant buffering capacity, such as histidine (preferably about 50 mM) or other zwitterionic buffers. In this manner, nucleic acid probes, sample nucleic acids, amplicons from samples, antigens, antibodies, or any other charged molecular species, may be addressed to specific microlocations of the device, and attached for use in various assay formats.

After addressing, the mesoporous synthetic hydrogel permeation layer devices may be utilized in a multitude of assay formats. For instance, devices which are addressed with nucleic acid probes or amplicons may be utilized in dot blot or reverse dot blot analyses as described in U.S. Pat. No. 5,051,380, base-stacking single nucleotide polymorphism (SNP) analysis as described in U.S. Ser. No. 09/291,129, SNP analysis with electronic stringency as described in U.S. Ser. No. 09/727,030, or in STR analysis as described in U.S. Pat. No. 6,207,373. In addition, such addressed devices may be utilized in formats for enzymatic nucleic acid modification, or protein-nucleic acid interaction, such as, e.g., gene expression analysis with enzymatic reporting as described in U.S. Ser. No. 09/710,200, anchored nucleic acid amplification as described in U.S. Pat. No. 6,238,868, or other nucleic acid modifications suitable for solid-phase formats including restriction endonuclease cleavage, endo- or exo-nuclease cleavage, minor groove binding protein assays, terminal transferase reactions, polynucleotide kinase or phosphatase reactions, ligase reactions, topoisomerase reactions, and other nucleic acid binding or modifying protein reactions.

In addition, the mesoporous synthetic hydrogel permeation layer devices are generally useful in immunoassay formats. For instance, the microlocations of the devices can be addressed with antigens (e.g., peptides, proteins, carbohydrates, lipids, proteoglycans, glycoproteins, etc.) in order to assay for antibodies in a bodily fluid sample by sandwich assay, competitive assay, or other formats. Alternatively, the microlocations of the device may be addressed with antibodies, in order to detect antigens in a sample by sandwich assay, competitive assay, or other assay formats. As the isoelectric point of antibodies and proteins can be determined fairly easily by experimentation or pH/charge computations, the electronic addressing and electronic concentration advantages of the devices may be utilized by simply adjusting the pH of the buffer so that the addressed or analyte species will be charged.

In addition to the simple active electronic matrix assay formats described above, formats utilizing specific pairing components as derivatization moieties for the attachment of biomolecules have also been described for active electronic matrix chip devices. These formats allow the simultaneous electronic addressing of several molecular species to a set of microlocations by using the specific pairing component (e.g., a pyranosyl RNA oligomer) to specifically bind to a complementary specific pairing component which has been previously attached to the permeation layer at the microlocation. These formats can dramatically reduce the amount of time necessary to create arrays of dozens of distinct binding entity compositions on an active electronic matrix array. The mesoporous synthetic hydrogel permeation layer devices of the invention would also be useful in these formats, which have been described for immunoassay-type arrays (see U.S. Ser. No. 09/783,763), and nucleic acid arrays (see U.S. Ser. No. 09/910,469).

All patents, patent applications, and published patent applications, and other publications referred to herein are hereby incorporated herein in their entirety by reference, as if they were fully reproduced herein.

EXAMPLES

The invention will now be described in greater detail by reference to the following non-limiting examples regarding the production and use of mesoporous synthetic polymer hydrogel permeation layers on active electronic matrix devices.

The recipes for buffers, solutions, and media in the following examples are described in J. Sambrook, E. F. Fritsch, and T. Maniatis, *Molecular Cloning: A Laboratory Manual*, 2 Ed., Cold Spring Harbor Laboratory Press, Cold Spring Harbor, N.Y., 1989.

Example 1

Exemplary Mesoporous Synthetic Hydrogel Permeation Layers

A. Acryloyl or Acrylamido Streptavidin Production

For incorporation into the mesoporous synthetic hydrogel permeation layer formulations, functionalized streptavidin derivatives with pendant acryl groups for incorporation into the polymer backbone were prepared. Streptavidin was derivatized with either an acrylamido group, or an amide-linked PEG 3400-ester-acryloyl group, according to the reaction scheme in FIG. 3. A N-acryloxysuccinimide was from Polysciences, Inc. and was used as received. α-Acryloyl, ω-N-hydroxysuccinimidyl ester of poly(ethylene glycol)—propionic acid, (M.W. 3400) (PEG-NHS) was from Shearwater Polymers, Inc. Streptavidin (SA) was purchased from Roche Molecular Biochemicals.

Native SA (165 mg) and an excess of NHS reagent (2.4 mg) were weighed out into a 15-ml disposable polypropylene cell culture tube. Sodium phosphate buffer (50 mM, pH 9, 12 ml) was added and the tube was vortexed briefly until all the solids were fully dissolved. The reaction was allowed to continue for 30 minutes in the dark. Products of streptavidin derivatization reactions were purified using a gel permeation column (HiPrep 26/10 GPC desalting column, Amersham Pharmacia Biotech) on an ÄKTA™ explorer HPLC system (Amersham Pharmacia Biotech). Elution was performed with sodium phosphate (50 mM, pH 7) at a rate of 10 ml/min. The first peak eluted between 10 and 24 ml and the second peak eluted above 30 ml. The second peak contained the free NHS and the excess acrylic acid that resulted from the SA derivatization reaction and from hydrolysis. All the fractions under the first peak were collected and concentrated on a rotaro-evaporator (SpeedVac) at 35° C. for six to seven hours. The concentrated solution was brought to room temperature and the protein concentration was measured by UV spectrophotometery at 280 nm. The concentration was adjusted to 35 mg/ml with deionized water.

The relative binding activities of unmodified SA, the N-acryl SA and the PEG-acryloyl SA were determined by a standard HABA assay. Unmodified SA had a HABA activity of 4.0, while the N-acryl SA had an activity of 3.8. The PEG-acryloyl SA had a relatively low activity of 3.0, possibly because of steric hindrance by the bulky PEG group. Because of its high retained binding activity, the N-acryl SA was utilized in the test formulations in a multi-batch production round as described in Example 3, and characterized in FIG. 10.

B. Activation of the Active Electronic Matrix Surface for Covalent Permeation Layer Anchoring In order to improve adhesion of the permeation layer to the active electronic matrix chip surface, the surface was silanized with an acryloyl moiety (Bind-Silane™ (3-methacryloxy-propyl-trimethoxysilane), product of Pharmacia Biotech). The active electronic matrix substrates were cleaned by argon plasma etching (100 W, for 30 min) and subsequently reacted with Bind Silane™ under vapor phase conditions. The vapor phase silanization was carried out in a polystyrene petri dish (150×15 mm). Five substrates were placed centro-symmetrically in the dish. Water (200 µl) was dispensed into the dish at 5 different perimeter locations. Bind Silane™(200 µl) was introduced into a small petri dish (35×10 mm) placed at the center of the large dish. The large petri dish was closed and the reaction was allowed to continue for 15 min at room temperature. The substrates were taken out and placed in glass petri dishes for subsequent heating in an oven at 90° C. for two hours.

One way of improving the effective function of a hydrogel as a permeation layer on an active electronic matrix chip is to have a strong adhesion between the hydrogel and the chip. By pre-treating the chip with silane having polymerizable groups which can subsequently be linked to a hydrogel via copolymerization, covalent linkage of the hydrogel to the substrate surface can be achieved. Bind Silane™ (3-methacryloxy-propyl-trimethoxysilane) is readily adsorbed onto the plasma cleaned active electronic matrix. The adsorbed silane subsequently reacts with the surface hydroxyl groups produced by the plasma etching on the area around the micro electrodes on the chip, leading to the formation of a stable silanized surface. In order to ensure complete surface attachment, the substrates after silane adsorption were heated at 90° C. for two hours in an air oven. This process results in the deposition and immobilization of an oligolayer (10-100 layers) of the silane. Similar studies on the vapor phase silanization of surfaces with (3-Aminopropyl)triethoxysilane (APS) have shown that adsorption of neat APS vapors results in a stable chemisorbed layer as well as a less stable physisorbed phase which can be removed by evacuation.

C. Exemplary Polymerization Mixture Formulations

Applicants developed several polyacrylamide-based permeation layer formulations for use on the active electronic matrix chips, a representative set of which are shown here. Although a single base polymer formula is used, alternative formulas could also be devised by those of skill in the art which would function well as the synthetic polymer component of the permeation layer. Similarly, although derivatized SA is copolymerized with the permeation layers described in these examples, other appropriate attachment moieties could be copolymerized with the permeation layer if non-biotin attachment [e.g., covalent attachment chemistries or salicyl hydroxamic acid/phenyl boronic acid chemistries] is to be utilized to address the microlocations. Likewise, the attachment moieties could be completely omitted if the permeation layer is to be later surface-derivatized, or an attachment layer is to be overlaid on a base permeation layer. For the reasons described above, however, it has been found to be preferable to copolymerize the attachment moieties into the permeation layer in a single layer.

The production of the acryl derivatives of SA is described above. Polyoxyethylene 100 stearyl ether (Brij 700) was purchased from Sigma. DMSO was an Aldrich product. Darocur® 4265 was supplied by Ciba. The monomer solutions were prepared by simply mixing the components together and vortexing, with the exception that Darocur was first dissolved in DMSO before addition to the other components. The basic formula used for the exemplary permeation layers described herein was an aqueous solution of:

total acrylamide/methylene bisacrylamide 18% w/v, 10 mol % bisacrylamide acryloyl-PEG-SA 14 mg/ml Darocur (added as 1.9% w/v solution in DMSO) 0.2% w/v Brij 700:
Formula 4012-1: 0 mg/ml
Formula 4012-2: 11 mg/ml
Formula 4012-3: 18 mg/ml
Formula 4006-1: 73 mg/ml Formula 4012-1 serves as a control synthetic polymer hydrogel composition in the following functional experiments, while 4012-2, 4012-3, and 4006-1 demonstrate the effect of increasing amounts of templating porogen.

D. Micromolding of the Synthetic Polymer Hydrogel Permeation Layers onto the Active Electronic Matrix Chip Surface A specially designed molding system was developed for the precise control of both the hydrogel layer thickness and the uniform distribution of UV radiation intensity. The system is comprised of a quartz microreaction mold with a precision-formed depression produced by standard microlithography techniques, and a UV light source assembly. A solution of the polymerization mixture (0.35 µl) was dispensed onto the mold surface and the microelectrode array substrate was compressed against the mold at a pressure of approximately 1 N. The polymerization was carried out in two steps, at an initial intensity of 700 µW/cm$^2$ for 15 sec followed by at a higher intensity of 70 mW/cm$^2$ for an additional 15 sec. The chip was withdrawn from the mold surface, washed in a stream of distilled water for 5 seconds and dried under a stream of nitrogen. This process was then repeated for the next chip.

The in situ polymerization and deposition of the hydrogel on the chip surface is illustrated by the reaction scheme in FIG. 4. The reaction molding is a controlled process which provides excellent thickness control of the molded layers. In addition, the system is designed to control the UV intensity, further allowing control of the polymerization rate and the degree of phase separation of the hydrogels. A stereo microscopic dark field image of a molded hydrogel on a 10×10 array substrate is shown in FIG. 2. The thickness control over a batch of 136 molded permeation layers was tested. The average thickness was quite uniform, being 1.8±0.3 µm. The polymerization conditions (UV intensity and exposure time) were optimized using a photo DSC. An optimum phase separation between the forming polymer and the surfactant template during polymerization has been achieved by using a two step UV curing process: an initial exposure to a low intensity (700 µW/cm$^2$ for 15 seconds), followed by a high intensity exposure (70 mW/cm$^2$ for 15 seconds.) Initiating the polymerization at a lower light intensity was also found to minimize the formation of gas bubbles from the exothermic polymerization reaction.

As one of ordinary skill in the art will appreciate, this process lends itself easily to automation, with robotics designed for the dispending of the monomer solution into the mold, positioning the chip over the mold, pressing the chip against the mold, irradiating the mold, and so forth. Thus, this type of process may be easily adapted to high-throughput production of the active electronic matrix chip devices.

In order to achieve complete removal of the surfactant, the substrates were washed extensively with water. They were placed in distilled water in a petri dish with shaking overnight, followed by rinsing thoroughly with running distilled water. This proved sufficient to remove the Brij surfactant material, leaving behind the mesostructured synthetic polymer hydrogel permeation layer.

Example 2

Figure 5:
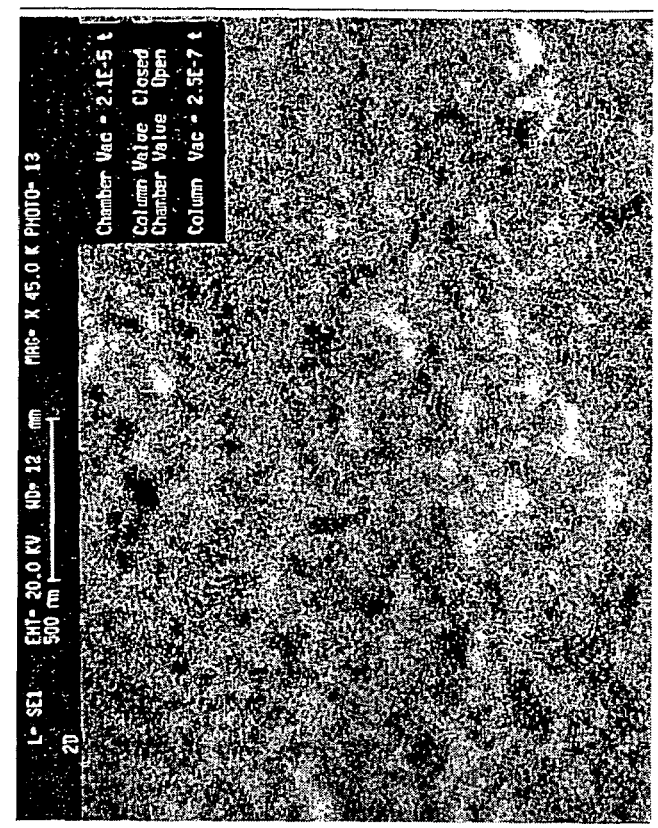
FIGS. 5 A and B: Scanning electron micrographs of the surface of a molded physically homogenous nanoporous polyacrylamide hydrogel permeation layer (4012-1) on a device. No templating agent (Brij surfactant) was used in this formulation. The surface of the gel appears relatively smooth in the 5,000×scan (5A), scale bar 5.00 μm. The surface shows only nanometer-scale pores in the 45,000× scan (5B), scale bar 500 nm. This is consistent with the estimated pore size in homogeneously polymerized acrylamide hydrogels reported elsewhere. These pores, less than 100 nm in size, are referred to as "Class I pores" herein.
Figure 5:
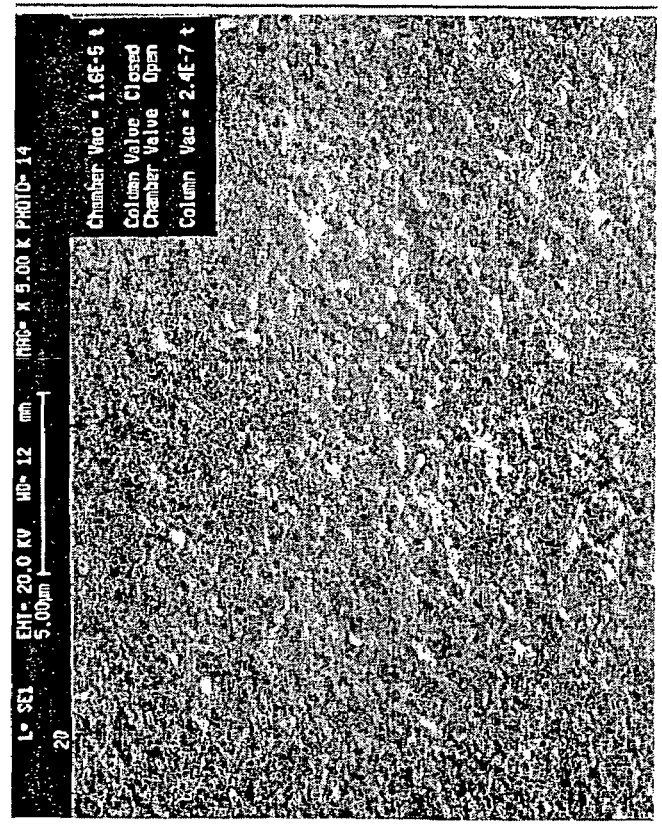
Figure 6:
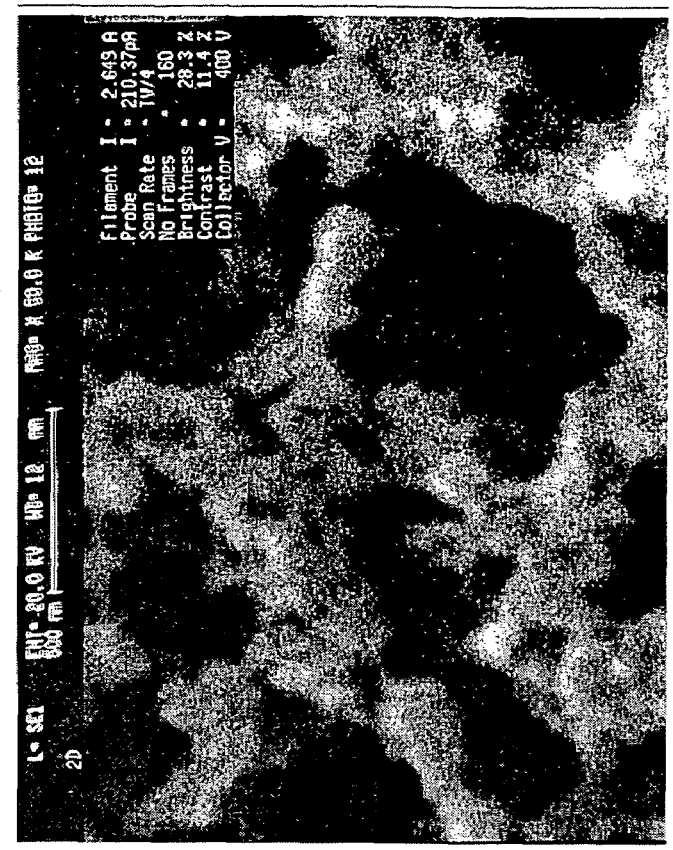
FIGS. 6 A and B: Scanning electron micrographs of the surface of a molded physically heterogeneous mesoporous polyacrylamide hydrogel permeation layer (4012-2) on a device. 11 mg/ml of templating agent (Brij 700 surfactant) was used in this formulation. The surface of the gel appears pitted in the 5,000×scan (6A), scale bar 5.00 μm. The surface shows 100-500 nanometer-scale pores in the 50,000×scan (6B), scale bar 500 nm. These pores, from about 100 nm to about 500 nm in size, are referred to as "Class II pores" herein.
Figure 6:
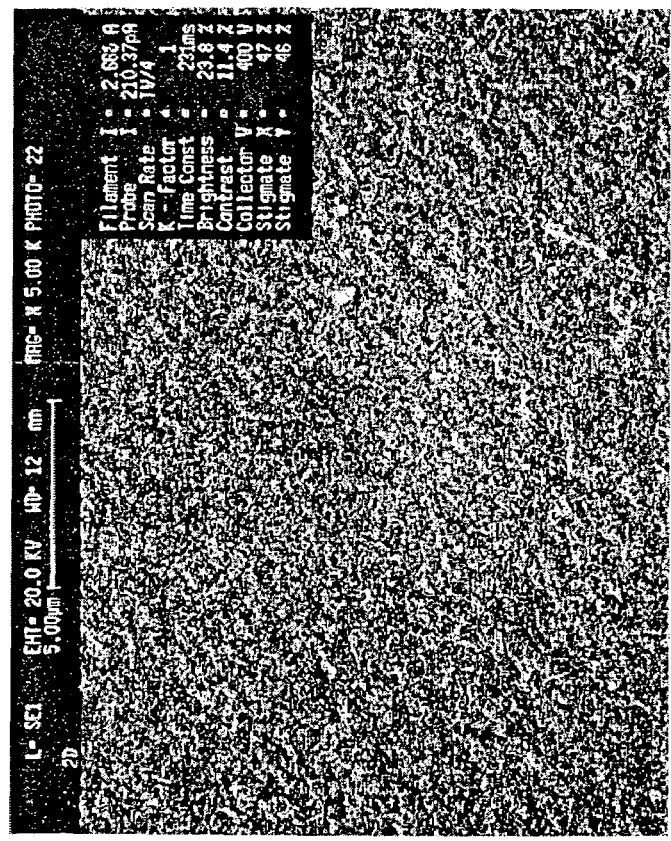
Figure 7:
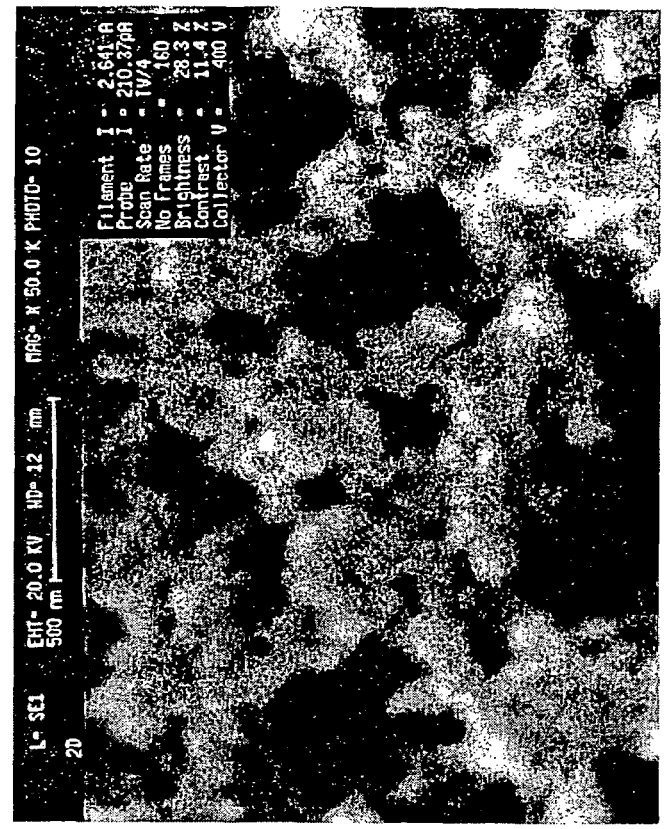
FIGS. 7 A and B: Scanning electron micrographs of the surface of a molded physically heterogeneous mesoporous/microporous polyacrylamide hydrogel permeation layer (4012-3) on a device. 18 mg/ml of templating agent (Brij 700 surfactant) was used in this formulation. The surface of the gel appears pitted and craggy in the 5,000×scan (7A), scale bar 5.00 μm. Micrometer scale pores are visible at this magnification. These pores, from about 500 nm to about 2.00 μm, are referred to as "Class III pores" herein. The surface shows class II pores in the 50,000×scan (7B), scale bar 500 nm.
Figure 7:
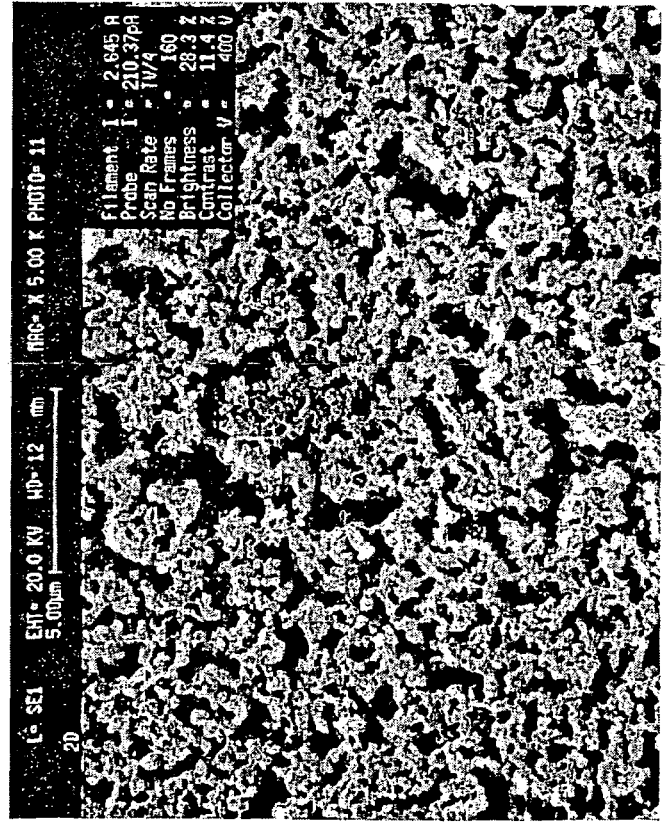
Figure 8:
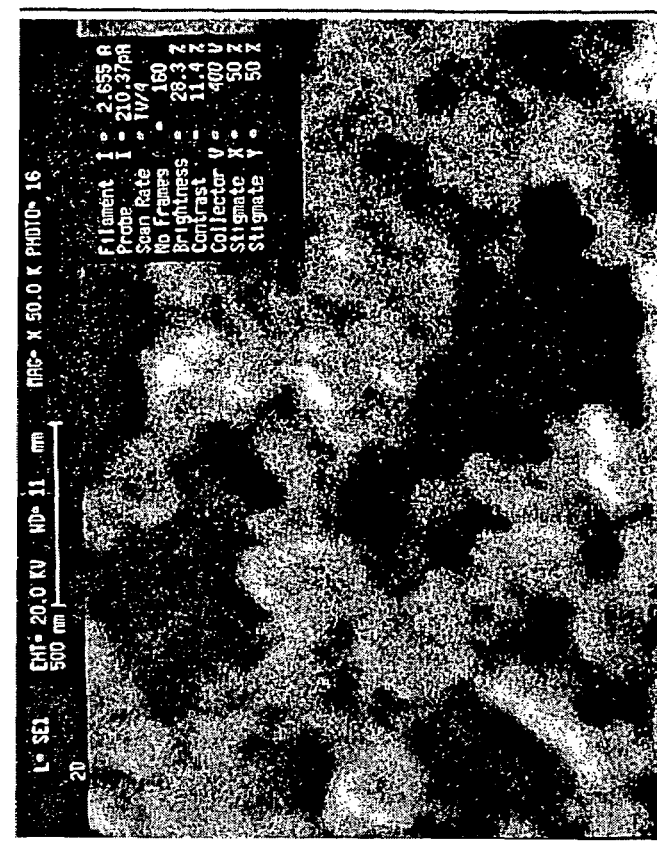
FIGS. 8 A and B: Scanning electron micrographs of the surface of a molded physically heterogeneous mesoporous/microporous polyacrylamide hydrogel permeation layer (4006-1) on a device. 73 mg/ml of templating agent (Brij 700 surfactant) was used in this formulation. The surface of the gel appears pitted and craggy in the 5,000×scan (8A), scale bar 5.00 μm, displaying class III pores. The surface shows class II pores in the 50,000×scan (8B), scale bar 500 nm.
Figure 8:
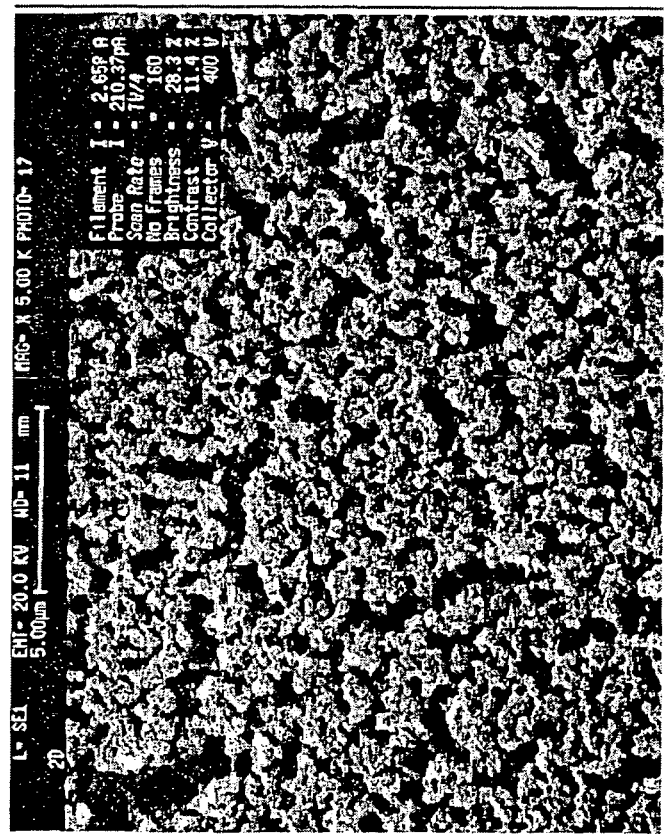

Scanning Electron Microscopy of the Mesoporous Synthetic Polymer Hydrogel Permeation Layer Structure The morphology of the mesoporous synthetic polymer hydrogel permeation layers was examined using a scanning electron microscope (SEM). Samples for SEM were prepared by gradual exchange of the water for ethanol in a gradient mode and subsequent drying by critical point drying technique with supercritical $CO_2$. This procedure has been reported to maintain the gel structure of the polymer with very little alteration. The scanning electron micrographs are shown in FIGS. 5 A & B (4012-1), 6 A & B (40012-2), 7 A & B (4012-3), and 8 A & B (4006-1). These micrographs clearly show the microstructure of the gels in the 5,000×scan, and show the mesostructure of the gels in the 45,000×scan. From these pictures, the physically heterogeneous nature of the mesoporous synthetic polymer hydrogel permeation layers is evident, especially when compared to the relatively physically homogeneous nature of 4012-1.

When examined under 5,000×magnification, 4012-1 (no pore template) appeared to have a relatively smooth, non-porous morphology when compared to the other permeation layers. 4012-3 and 4006-1 exhibited a very porous structure with a wide distribution of larger pores. The pores in the gel structures can be roughly divided into three classes:

Class I—pores of size less than 100 nm (nanoporous)
Class II—pores in the order of 100-1000 nm, mainly in the range of 100-500 nm (mesoporous)
Class III—pores in the order of 1-2 um.

The large pores Class III (micron order) were not obvious on formulation #4012-2, although Class II pores did appear to be present at this magnification.

The higher magnification images (45,000×) of these permeation layers demonstrated that the fine pore structures of the mesoporous synthetic polymer hydrogel permeation layers are very similar, with 4012-2, 4012-3, and 4006-1 showing a mesoporous structure. The higher template concentration synthetic polymer hydrogel permeation layers 4012-3 and 4006-1 also show micropores, separating areas of mesoporous permeation layer material. Such micropores probably indicate the aggregation of surfactant micelles above a certain concentration in the polymerization mixture, which would account for the sharp difference in morphology between 4012-2 and 4012-3, but relatively unchanged morphology between 4012-3 and 4006-1.

Thus, the synthetic polymer hydrogel permeation layers may be classified in three groups: 4012-1 is nanoporous (Class I), 4012-2 is mesoporous (Class II), while 4012-3 and 4006-1 are mesoporous and microporous (Class II and III).

Example 3

Use of θ to Quantify the Porosity of Mesoporous Synthetic Polymer Hydrogel Permeation Layers As is shown by the scanning electron micrographs, the porosity of synthetic polymer hydrogels can be varied by varying the amount of template porogen, such as Brij surfactant, used in the polymerization mixture. Although the SEM micrographs are useful to qualitatively and quantitatively evaluate the morphology of the mesoporous synthetic polymer hydrogel permeation layers, a less labor intensive quantitative porosity measurement was desired. Towards that end, dark field microscopy was used to quantify the morphological changes due to phase separation.

A dimensionless parameter, θ (theta), was used to express the degree of phase separation, or porosity, based on light scattering measurements under the dark field microscope. The dimensionless degree of phase separation (θ) was determined by integrating the dark filed light intensity readings a dry hydrogel layer on the test chip ($\lambda$), a standard layer ($\lambda_S$) with a medium degree of phase separation and a non-phase separated, or solid, layer ($\lambda_0$) on the Leica INM 100 dark field microscope, and was computed with the following formula. When $\lambda_0 \ll 1$ the equation can be simplified:

$$\theta \equiv \frac{\lambda - \lambda_0}{\lambda_S - \lambda_0} \approx \frac{\lambda}{\lambda_S}$$

An example of a surface which would approach the an ideal non-phase separated layer would be a very smooth surface, such as vapor-deposited platinum on an electronics grade silicon wafer. The change in θ of polymer layers as a function of porosity was measured for 4012-1, 4012-2, 4012-3, and 4006-1. The standard layer was a polyacrylamide hydrogel of the following composition (composition S):

Acrylamide: Bisacrylamide 19:1 (mol/mol)
Total monomer content 20% by weight

Under the illumination conditions used in the examples, $\lambda_S$ was 60±1.5, which was used for these experiments. The θ value for 4012-1, polymerized without template porogens, was 1.35. Addition of Brij to the formulation increases the phase separation or porosity, and thus increase the θ value. Formulation 4012-2 had a θ of 3.06, 4012-3 had a θ of 3.27 and 4006-1 had a theta of 3.00. Thus, all of the exemplary mesoporous synthetic polymer hydrogel permeation layers had θ's in the range 3.0-3.5.

Several micromolded permeation layers made from different batches of polymerization mixtures were tested using the above technique. The permeation layer formulation was the same as 4006-1, except that N-acryl-SA was utilized instead of acryloyl-PEG-SA. The results are shown in the chart of FIG. 10. The θ porosity measurement is very consistent over twenty different batches (mean θ of 3.63±0.07). Interestingly, the use of N-acryl-SA, increased the relative phase separation, or porosity, of the permeation layer when compared to acyloyl-PEG-SA. This demonstrates the impact that subtle changes in the polymerization formula can have on porosity. These data further show that mesoporous synthetic hydrogel permeation layers can be molded onto active electronic matrix devices in a consistent fashion. Likewise, the consistency of the light-scattering measurement technique is also validated.

Example 4

Comparison of a Mesoporous Synthetic Polymer Hydrogel Permeation Layer to a SA-Agarose Permeation Layer In order to compare the performance of a mesoporous synthetic polymer hydrogel permeation layer to Nanogen's current SA-agarose permeation layer (MSP), a single nucleotide polymorphism assay (SNP assay) was performed using active electronic matrix chips with the two layers. In the SNP1 assay, an ||120 nt biotinylated amplicon, 5 nM in 50 mM histidine, was electronically addressed to microlocations on both chips at a constant potential of 2.1 V for 2 minutes. Cy 3 labeled reporter oligonucleotides for the C-allele and Cy 5 labeled reporter oligonucleotides for the T-allele, both 12 nt long, were then passively hybridized on the chip, at a concentration of 500 nM in a high salt buffer (50 mM sodium phosphate, 500 mM sodium chloride).

Figure 11:
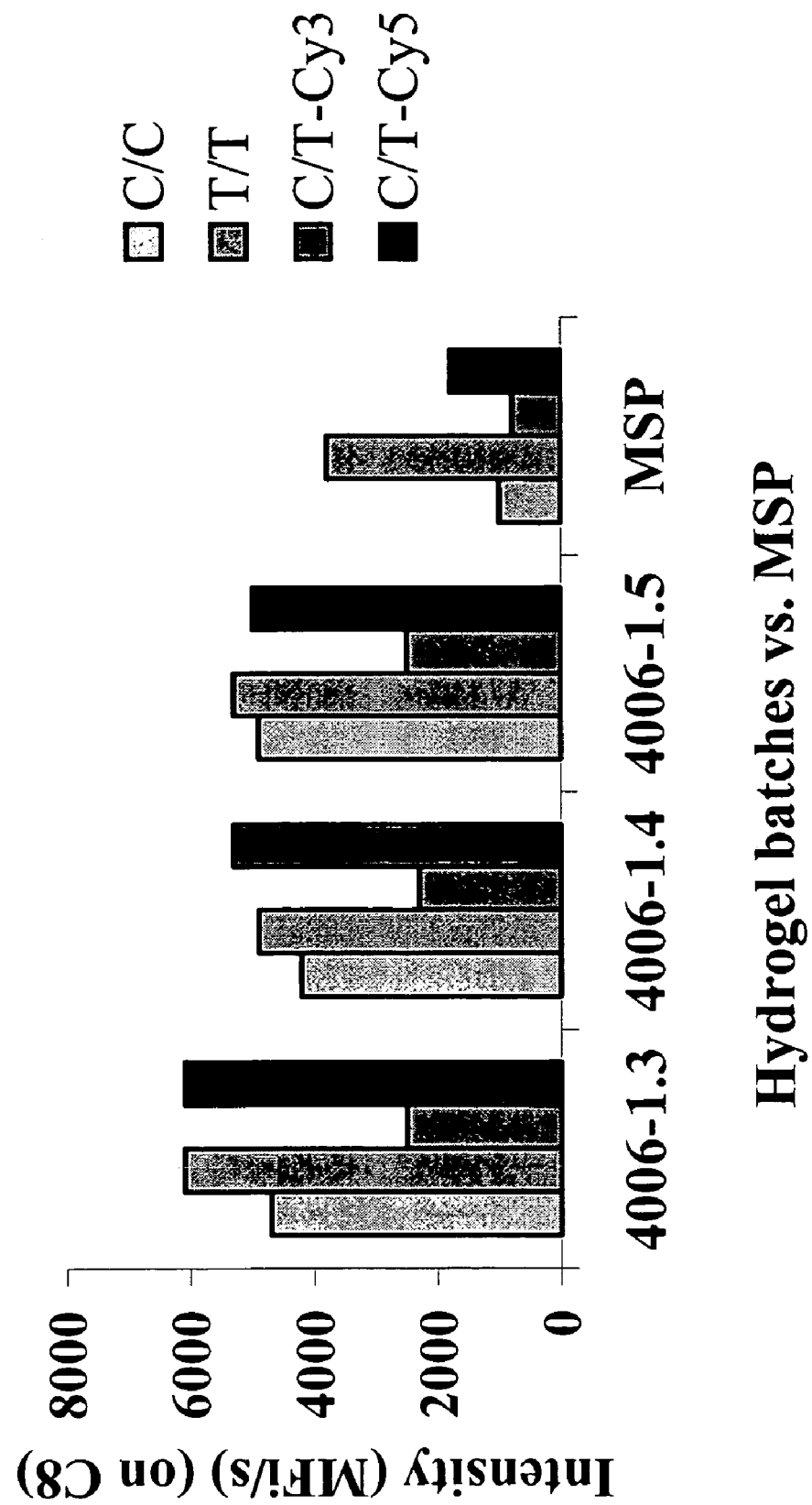
FIG. 11: A chart showing mean fluorescent intensity (MFI) readings for the SNP1 assay described in Example 4, performed on three active electronic matrix chip device with 4006-1 permeation layers, and the results of the same assay performed on a standard SA-agarose permeation layer chip. Note that the fluorescent intensity readings on the 4006-1 chips are generally higher than those on the SA-agarose chip, and that both allele probes (C-allele-Cy-3, and T-allele-Cy-5) give good readings, allowing the easy identification of heterozygous amplicon mixtures.

The results are shown in FIG. 11. The mean fluorescent intensity readings for a SNP1 assay performed on three active electronic matrix chip device with 4006-1 permeation layers were generally above 2000 for all three chips tested. Both allele probes (C-allele-Cy-3, and T-allele- Cy-5) were detected well, allowing the easy identification of heterozygous amplicon samples. As compared to the results of the same assay performed on a standard SA-agarose permeation layer chip, the 4006-1 mesoporous synthetic polymer hydrogel permeation layer formulation exhibited improved signal intensity in the SNP assay. The fluorescence intensity readings on the 4006-1 chips were generally higher than those obtained using the SA-agarose chip.

Similar SNP assays of clinical interest were run on twenty 4006-1 N-acryl-SA chips, using amplicons from sample nucleic acids of about 150 to about 250 nt in length, and base-stacking format reporter probes. In general, biotinylated amplicons at relatively low concentrations were electronically addressed to microlocations on the active electronic matrix chips in 50 mM histidine buffer. Stabilizer probes and base-stacking stabilizable allele specific reporter probes (Cy-3 and Cy-5 labeled) were then passively hybridized to the addressed amplicons under higher concentration and high-salt conditions. Mean fluorescent intensity measurements were then taken after thermal stringency was applied. The performance results for the assays are shown in the table below:

| SNP | Genotype | # of Exp. | Correct calls | Incorrect calls | No calls | Discrimination ratio |
| --- | --- | --- | --- | --- | --- | --- |
| SNP2 | Mut/mut (red) | 20 | 18 | | 2 | ≧21 |
| | Mut/wt | 20 | 18 | | 2 | |
| | Wt/wt (green) | 20 | 18 | | 2 | ≧50 |
| SNP3 | Wt/wt (green) | 20 | 18 | | 2 | ≧50 |
| | Wt/wt (green) | 20 | 18 | | 2 | ≧40 |
| | Mut/wt | 20 | 18 | | 2 | |
| SNP4 | Wt/wt (green) | 20 | 18 | | | ≧100 |
| | Mut/mut (red) | 20 | 20 | | | ≧50 |
| | Mut/wt | 20 | 20 | | | |
| SNP5a | Wt/wt (green) | 14 | 14 | | | ≧30 |
| | Wt/wt | 14 | 14 | | | ≧30 |
| | Mut/wt | 14 | 14 | | | |
| | Mut/wt | 14 | 14 | | | |
| | Wt/wt (green) | 14 | 14 | | | ≧30 |
| | Wt/wt (green) | 14 | 14 | | | ≧30 |
| | Mut/wt | 14 | 14 | | | |
| SNP5b | Wt/wt (green) | 14 | 14 | | | ≧30 |
| | Wt/wt (green) | 14 | 14 | | | ≧30 v |
| | Mut/wt | 14 | 14 | | | |
| | Mut/wt | 14 | 14 | | | |
| | Wt/wt (green) | 14 | 14 | | | ≧30 |
| | Wt/wt (green) | 14 | 14 | | | ≧30 |
| | Mut/wt | 14 | 14 | | | |
| SNP6a | Genotype A | 20 | 20 | | | |
| | Genotype B | 20 | 20 | | | ≧100 |
| | Genotype C | 20 | 20 | | | ≧30 |
| | Genotype D | 20 | 20 | | | ≧60 |
| SNP6b | Genotype A | 20 | 20 | | | ≧70 |
| | Genotype B | 20 | 20 | | | ≧60 |
| | Genotype C | 20 | 20 | | | ≧40 |

As can be seen from the results of the above table, the 4006-1 active electronic matrix chips performed very well in the SNP assays tested, with excellent discrimination ratios between alleles (Cy-3 and Cy-5 labeled reporter oligos). SNP2 and SNP3 were tested in a multiplexed assay format, in which both amplicons were individually amplified from a nucleic acid sample, and then simultaneously addressed to the same microlocation and tested by hybridization with the reporter oligomers sequentially. The fluorescence results were read sequentially, after applying thermal stringency to remove one set of reporter oligomers. The two no-calls for SNP 2 were later verified to be amplification failure in the particular nucleic acid sample.

Example 5

Comparison of Small and Medium Length Nucleic Acid Binding in Mesoporous Synthetic Polymer Hydrogel Permeation Layers The commercially available Nanogen NanoChip® Molecular Biology Workstation (Nanogen, Inc.) chip addressing module is able to address four chips at the same time, under essentially the same conditions. Thus, for synthetic polymer hydrogel permeation layer comparison experiments, four chips with four different acryloyl-PEG-SA hydrogel formulations (4012-1, 4012-2, 4012-3, and 4006-1) were placed into the addressing module and addressed side-by side according to the following procedures:

The ability of relatively small nucleic acids (under 50 nt in length) to bind to copolymerized SA attachment moieties in the mesoporous synthetic polymer hydrogel permeation layers as compared to nanoporous synthetic polymer hydrogel permeation layers (such as normal crosslinked acrylamide hydrogels) was ascertained by a direct binding assay. This is a direct measure of the degree of the binding of relatively small nucleic acids, as would be used for capture probes, onto the synthetic polymer hydrogel permeation layer chips. A fluorophore labeled 46-nt DNA, biotinylated at the 5' end, 5 nM, was addressed electronically to the chip (2.0 v; 60 seconds). As the nucleic acids were directly labeled with the fluorophore, fluorescence intensity on the chip was a direct measure of the degree of DNA binding. The results of the assay are shown in the diamond-marked line in FIG. 12.

In order to measure the ability of medium sized nucleic acids (about 60-150 nucleotides in length) to copolymerized SA attachment moieties in the mesoporous synthetic polymer hydrogel permeation layers as compared to nanoporous synthetic polymer hydrogel permeation layers, a dot-blot assay was used. A 114 nt single stranded DNA amplicon, biotinylated at the 5' end, 5 nM was electronically addressed to the chips under the same electronic conditions. A fluorophore labeled reporter oligonucleotide (12 bp) was then hybridized passively to the amplicons bound to the chip. The fluorescence intensity results for the different synthetic polymer hydrogel permeation layer formulations are shown by the square-marked in FIG. 12.

Thus, nanoporous hydrogels such as #4012-1, seem to favor binding interactions with shorter oligonucleotides. The MFI readings for the 114-mer were almost 3 fold less than that of a 46-mer. Binding of the longer DNA (114-mer) increased drastically (~4 fold) when a mesoporous permeation layer was utilized (4012-2, 4012-3, and 4006-1). Increased signal intensity more directly correlates with increased porosity ($\theta$) until a $\theta$ greater than about 3.0 (i.e., composition 4006-1). These data suggest that maximal performance for this type of assay may be obtained using a mesoporous synthetic hydrogel permeation layer with a porosity with a $\theta$ from about 2 to about 3. In these data, the mesoporous synthetic polymer hydrogel permeation layers showed a clear advantage over the nanoporous synthetic polymer hydrogel permeation layer when addressing amplicons of a size often used for SNP, STR, or gene expression analysis. This may be the result of increased accessibility of the immobilized SA to the long DNA via the larger pores.

The shorter DNA (46-bp), however, showed a slight decrease in binding with increased porosity. Results of additional experiments suggest that, under electronic addressing conditions, shorter DNA may permeate through the mesoporous synthetic polymer hydrogel permeation layer without having sufficient time to achieve streptavidin-biotin complexation. This has further been confirmed by passive DNA binding experiments (i.e., the absence of any applied electric field) wherein the short DNA bound equally well to both mesoporous and nonporous layers.

Example 6

Comparison of Primer Extension Reporting Linearity in Mesoporous Synthetic Polymer Hydrogel Permeation Layers In multiplexed assays in which the presence and/or quantity of a large number of amplicons are to be detected, primer extension detection of the amplicons is desirable to avoid reporter/stabilizer probe dimerization. Thus, to test the four synthetic polymer hydrogel formulations, electronic hybridization of a target deoxyribonucleic acid (78 nt) was performed, followed by enzymatic reporting on the chips. Initially, a capture oligonucleotide (500 nM) complementary to the target DNA sequence was loaded on the chip, and subsequently electronically hybridized to different concentrations (0.5 nM, 1.0 nM, 2.0 nM, 4.0 nM, 8.0 nM, and 16.0 nM) of the target. Enzymatic primer extension using dNTPs containing dCTP-Cy5 was used to quantify the degree of target hybridization.

In these assays, the fluorescence intensity measured on the chip is influenced by two main factors: the efficiency of binding of the DNA on the chip, and the efficiency of capture primer extension by the polymerase enzyme. The extension reaction depends on the porosity of the polymer surface and subsequent accessibility to the DNA in the matrix. The results are shown in FIG. 13.

As shown in the FIGS. 13, the nanoporous synthetic polymer hydrogel permeation layer, 4012-1, showed a relatively linear increase in MFI for target concentrations of up to ~2 nM. Further increase in concentration did not increase the signal intensity. This phenomenon may be due to a combined effect of 1) a decrease in target hybridization and/or 2) a decrease in access to the hybridized nucleic acid by the polymerase enzyme. In contrast, the mesoporous synthetic polymer hydrogel permeation layers (4012-2, 4012-3, and 4006-1) exhibited a good linear increase in signal intensity with increase in target concentration over the entire concentration range spanning two orders of magnitude. This type of linear response curve is desirable for applications in which quantitative relationships between the target nucleic acids are being studied, such as in gene expression analysis, or in viral load/population studies.

Example 7

Comparison of Various Synthetic Hydrogel Permeation Layer Formulations Using the Light-Scattering $\theta$ Technique and Reverse Dot-Blot Nucleic Acid Assays In order to explore the effect of various amounts of template porogen on the porosity of the synthetic polymer hydrogel permeation layers, as measured by $\theta$, permeation layers were formed on active electronic matrix chip substrates as described above using the basic polymerization mixture with various amounts of Brij 700 surfactant added. Concentrations (mg/ml) used were: 0.0, 3.9, 9.3, 18.6, 55.8, 71.3, 80.6, 102.3, and 170.4. As the critical micelle concentration for most Brij surfactants is 1 mg/ml, 3.9 was the lowest concentration used. The standard $\lambda$ used for the $\theta$ measurement was 60±1.5. As seen in FIG. 14, the synthetic polymer hydrogel permeation layers showed a rather marked increase in phase separation, or porosity, throughout the lower concentrations of surfactant template. This leveled off at about 80 mg/ml Brij 700 surfactant to a maximum $\theta$ range of about 3.5. This is consistent with the observations of porosity by SEM examination of the permeation layers, as described in Example 2.

Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the appended claims.

We claim:

1. A method for forming a permeation layer on an array of microelectrodes comprising the steps of:
   attaching a linker to a surface of the array of microelectrodes by treating the surface with a linker by vapor deposition;
   providing a polymerization solution comprising:
     at least one monomer having a polymerizable moiety;
     a modified streptavidin derivative;
     a surfactant;
     and a cross-linking agent;
   contacting the surface of the array with the polymerization solution;
   polymerizing the polymerization solution on the surface of the array to form a permeation layer, wherein the permeation layer is attached to the surface of the array through the linker, and
   removing the surfactant from the permeation layer, thereby creating void spaces in the permeation layer.

2. The method of claim 1, wherein the streptavidin derivative is modified with an acryloyl functional group.

3. The method of claim 2, wherein the modified streptavidin derivative is formed by reacting streptavidin with N-acryloxysuccinimide.

4. The method of claim 1, wherein the streptavidin derivative is modified with PEG-ester linked acrylate moieties.

5. The method of claim 1, wherein the polymerization solution is placed in a mold cavity.

6. The method of claim 5, wherein the mold cavity comprises a bottom and at least one side and wherein the array and mold cavity form a closed volume for the polymerization mixture that is in contact with at least one microelectrode in the array of microelectrodes.

7. The method of claim 1, wherein the surfactant is a Brij surfactant.

8. The method of claim 1, wherein the surfactant is a micelle-forming surfactant.

9. The method of claim 1, wherein the surfactant is removed with a solvent.

10. The method of claim 9, wherein the solvent does not significantly alter a porous structure of the permeation layer.

11. The method of claim 1, wherein the polymerizable moiety is selected from the group consisting of alkenyl, vinyl, allyl, homoallyl, alkynyl, epoxide, cyclic anhydride, ester, ether, and alkylene moieties.

12. The method of claim 1, wherein the at least one monomer having a polymerizable moiety is an acryloyl or acrylamido monomer.

13. The method of claim 12, wherein the acrylamido monomer is selected from the group consisting of acrylamides, N-substituted acrylamides, N-substituted methacrylamides, and methacrylamide.

14. The method of claim 12, wherein the acrylamido monomer is methacrylamide.

15. The method of claim 1, wherein the cross-linker is methylene bisacylamide.

16. The method of claim 1, wherein the polymerization solution further comprises a free radical initiator.

17. The method of claim 16, wherein the free radical initiator is a photoinitiator, and wherein the polymerization step comprises irradiating the polymerization solution with radiation at a wavelength appropriate to activate the photoinitiator.

18. The method of claim 1, wherein the permeation layer is approximately 1 nanometer to 100 microns thick.

19. The method of claim 1, wherein the array of microelectrodes comprises electrodes made from a material selected from the group consisting of platinum silicide, tungsten silicide, titanium silicide, and gold silicide.

20. The method of claim 1, wherein the array of microelectrodes comprises electrodes made from a material selected from the group consisting of aluminum, copper, carbon, iron, silver, gold, palladium, platinum, titanium, tungsten, polysilicon, and indium tin oxide.

21. The method of claim 1, wherein the array of microelectrodes comprise platinum electrodes.

22. The method of claim 1, further comprising the step of treating the array with an argon plasma before attaching the linker.

23. method of claim 1, further comprising insulating material that overlays the array of microelectrodes, and wherein the insulating material has been removed to expose at least one microelectrode in the array of microelectrodes.

24. The method of claim 23, wherein the insulating material has been removed to expose all of the microelectrodes in the array of microelectrodes.

25. The method of claim 23, wherein the insulating material is silicon dioxide.

26. The method of claim 1, wherein the linker is covalently attached to the surface.

27. The method of claim 1, wherein the linker has a acryloyl moiety.

28. The method of claim 27, wherein the linker is 3-methacryloxy-propyl-trimethowysilane.

29. The method of claim 1, wherein the linker is selected from the group consisting of acrylates, methacrylates, acrylamides, methacrylamides, allyl derivatives, amino derivatives, and epoxy derivatives.

30. The method of claim 1, wherein the linker is selected from the group consisting of APS, AEAPS, AHAPS, MOTS, and AMPTS.

31. The method of claim 1, wherein the permeation layer forms a mesoporous structure upon removal of the surfactant.

32. The method of claim 31, wherein the mesoporous structure defining pores that are between about 100 nm and 1000 nm in diameter.

33. The method of claim 1, wherein the permeation layer forms a nanoporous structure upon removal of the surfactant.

34. The method of claim 1, wherein the permeation layer forms a microporous structure upon removal of the surfactant.

* * * * *